(12) United States Patent
Saito et al.

(10) Patent No.: US 10,130,320 B2
(45) Date of Patent: Nov. 20, 2018

(54) X-RAY CT APPARATUS AND IMAGE DIAGNOSTIC APPARATUS

(71) Applicant: TOSHIBA MEDICAL SYSTEMS CORPORATION, Otawara-Shi (JP)

(72) Inventors: Yasuo Saito, Nasushiobara (JP); Shinsuke Tsukagoshi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/953,125

(22) Filed: Nov. 27, 2015

(65) Prior Publication Data

US 2016/0073986 A1    Mar. 17, 2016

Related U.S. Application Data

(63) Continuation of application No. PCT/JP2014/064032, filed on May 27, 2014.

(30) Foreign Application Priority Data

May 27, 2013  (JP) ................. 2013-111239

(51) Int. Cl.
   *A61B 6/00*    (2006.01)
   *A61B 6/03*    (2006.01)
(52) U.S. Cl.
   CPC .............. *A61B 6/463* (2013.01); *A61B 6/032* (2013.01); *A61B 6/035* (2013.01); *A61B 6/469* (2013.01);
   (Continued)
(58) Field of Classification Search
   CPC .................................. A61B 6/463; G06K 9/00
   See application file for complete search history.

(56) References Cited

U.S. PATENT DOCUMENTS

| | | | |
|---|---|---|---|
| 5,891,030 A * | 4/1999 | Johnson ................. | A61B 6/032 128/920 |
| 6,798,861 B2 * | 9/2004 | Shiota ................... | A61B 6/4085 378/17 |

(Continued)

FOREIGN PATENT DOCUMENTS

| | | |
|---|---|---|
| JP | 08-166995 | 6/1996 |
| JP | 2000-175903 | 6/2000 |

(Continued)

OTHER PUBLICATIONS

International Search Report dated Jun. 24, 2014 in PCT/JP2014/064032 filed May 27, 2014 (with English translation).

(Continued)

*Primary Examiner* — Anand Bhatnagar
(74) *Attorney, Agent, or Firm* — Oblon, McClelland, Maier & Neustadt, L.L.P.

(57) ABSTRACT

In an X-ray CT apparatus of an embodiment, an X-ray tube emits X-rays. A detector detects the X-rays emitted from the X-ray tube and having passed through a subject. Processing circuitry collects projection data based on data detected by the detector. The Processing circuitry generates a reconstructed image from the projection data. A display displays a display image based on the reconstructed image. A input circuitry receives an operation to rotate a first display image based on a first reconstructed image generated by the processing circuitry on a screen of the display, and specify a certain region on a second display image whose axis is in a direction different from a slice direction. The processing circuitry generates a second reconstructed image from the projection data, having higher resolution than that of the first display image, for the certain region.

21 Claims, 17 Drawing Sheets

(52) U.S. Cl.
CPC .......... *A61B 6/5205* (2013.01); *A61B 6/5223* (2013.01); *A61B 6/465* (2013.01)

(56) References Cited

U.S. PATENT DOCUMENTS

| | | | |
|---|---|---|---|
| 6,850,586 B2* | 2/2005 | Cahill | G01N 23/046 378/8 |
| 7,492,967 B2* | 2/2009 | Toki | A61B 6/032 382/299 |
| 7,583,782 B2* | 9/2009 | Yamazaki | A61B 6/032 378/147 |
| 8,285,023 B2 | 10/2012 | Tsujii et al. | |
| 8,792,965 B2* | 7/2014 | Ning | A61B 6/032 378/37 |
| 2004/0190674 A1 | 9/2004 | Tsukagoshi | |
| 2005/0180540 A1 | 8/2005 | Mukumoto | |
| 2007/0214017 A1 | 9/2007 | Profio et al. | |
| 2010/0034342 A1* | 2/2010 | Forthmann | A61B 6/032 378/15 |
| 2011/0044520 A1* | 2/2011 | Nakai | A61B 6/032 382/131 |
| 2013/0004048 A1 | 1/2013 | Tsujii et al. | |
| 2014/0313196 A1* | 10/2014 | Mistretta | A61B 6/032 345/424 |
| 2015/0173690 A1* | 6/2015 | Ning | A61B 6/032 600/427 |
| 2015/0238159 A1* | 8/2015 | Al Assad | A61B 6/5258 378/5 |
| 2016/0042537 A1* | 2/2016 | Ng | G06T 11/005 382/131 |
| 2016/0073974 A1* | 3/2016 | Saito | A61B 6/032 378/98.2 |

FOREIGN PATENT DOCUMENTS

| | | |
|---|---|---|
| JP | 2001-022964 | 1/2001 |
| JP | 2001-137231 | 5/2001 |
| JP | 2004-298247 | 10/2004 |
| JP | 2005-095328 | 4/2005 |
| JP | 2007-195970 | 8/2007 |
| JP | 2007-244860 | 9/2007 |
| JP | 2009-056032 | 3/2009 |
| JP | 2010-046360 | 3/2010 |
| JP | 2011-067687 | 4/2011 |

OTHER PUBLICATIONS

Written Opinion dated Jun. 24, 2014 in PCT/JP2014/064032 filed May 27, 2014.

Japanese Office Action for Japanese Application No. 2014-109537, dated May 22, 2018.

* cited by examiner

FIG. 7A
(A)
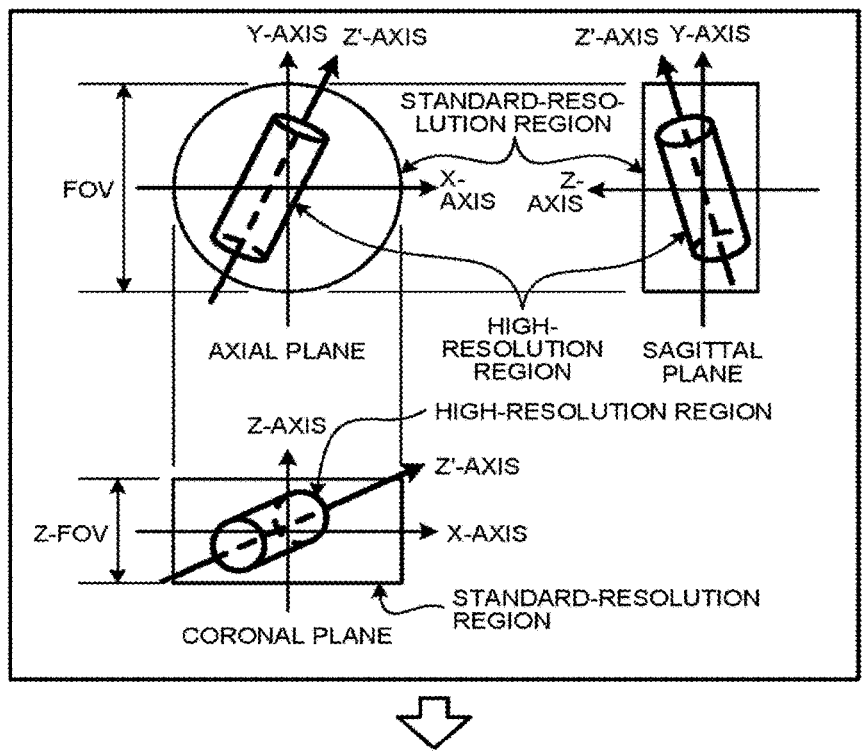
(B)
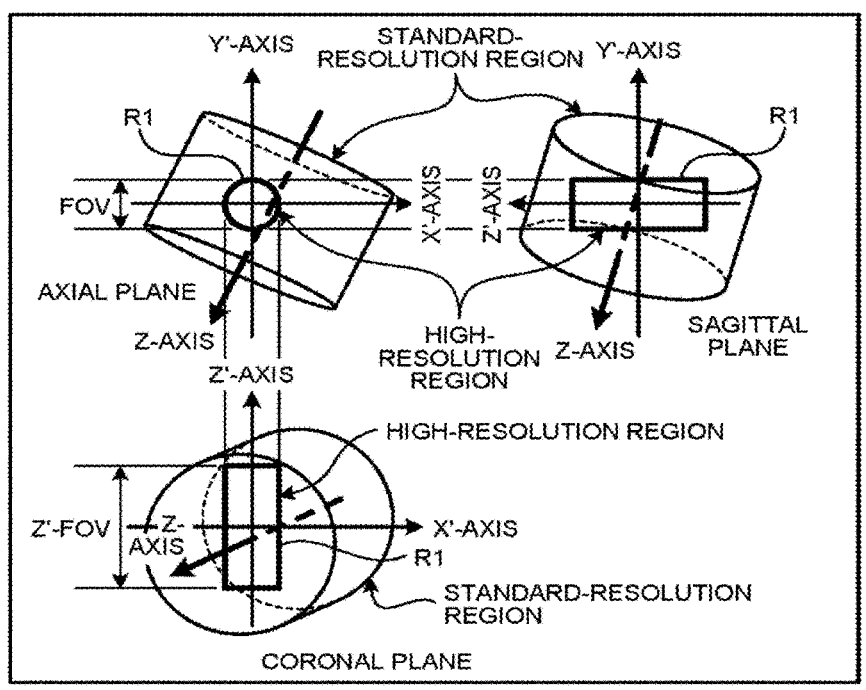

FIG.7B
(A)
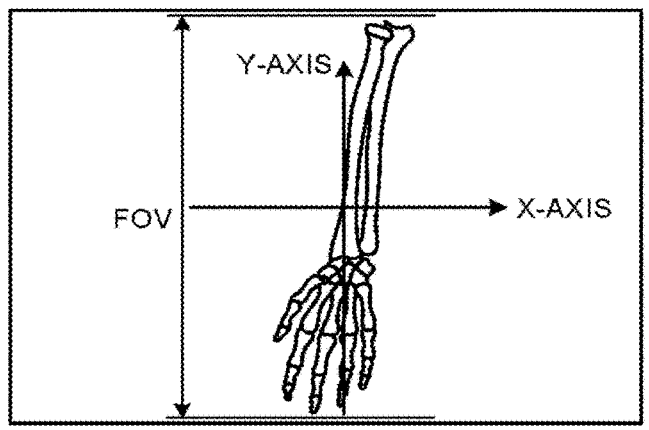
(B)
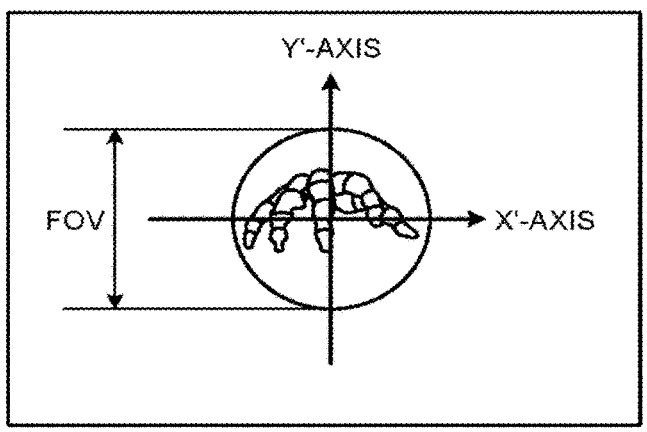
(C)
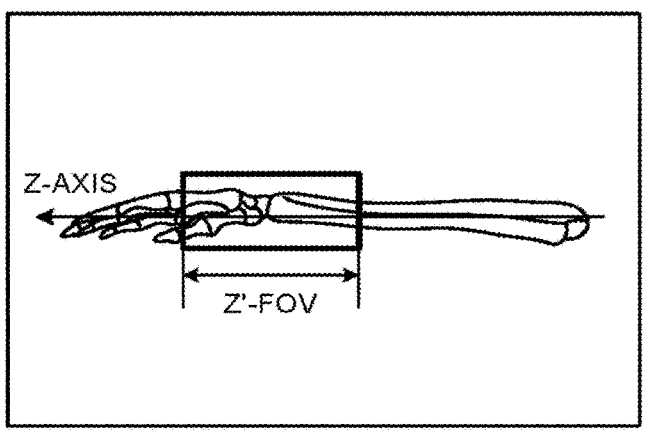

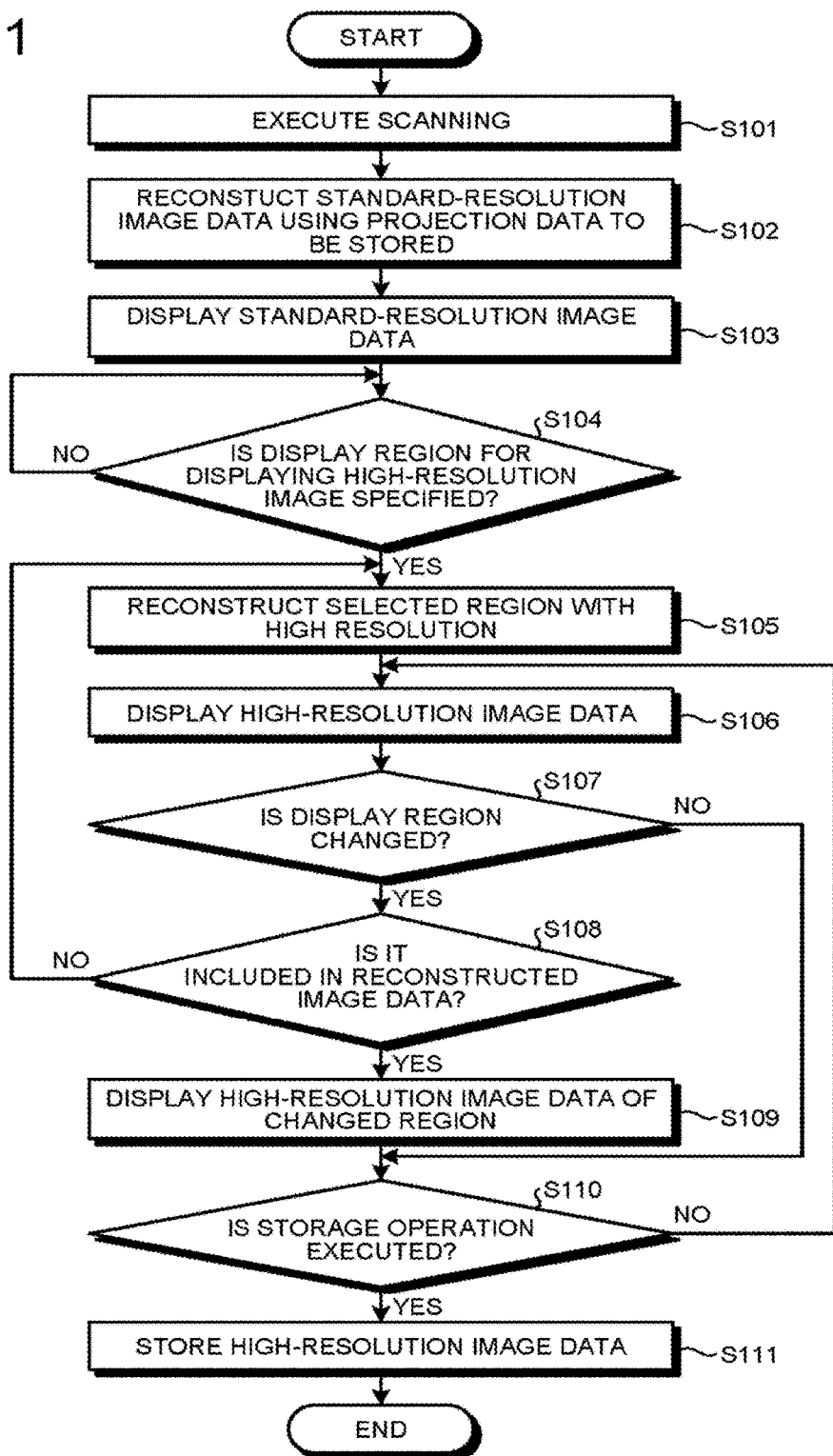

FIG.14
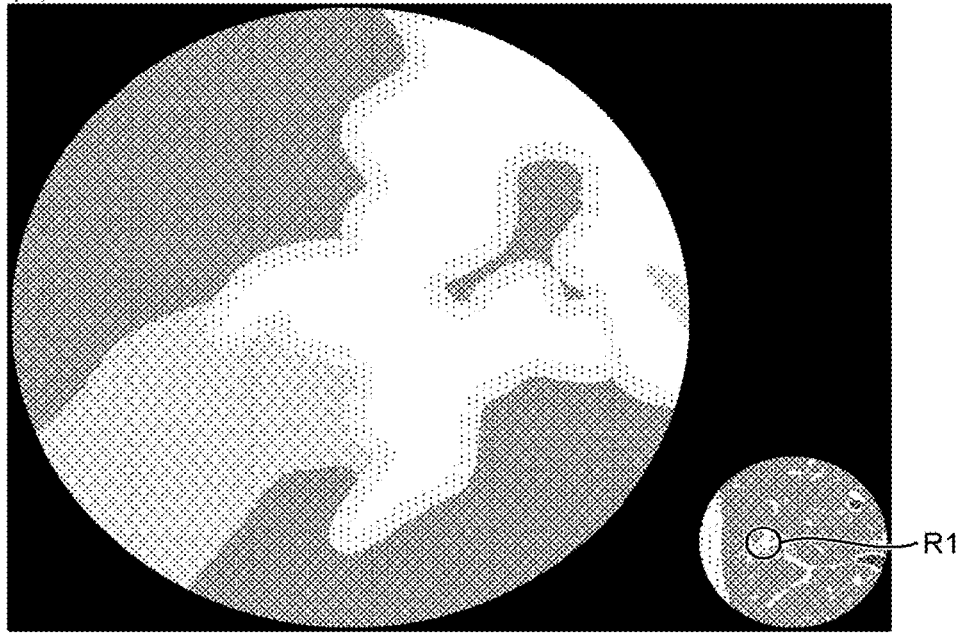
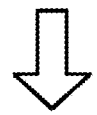
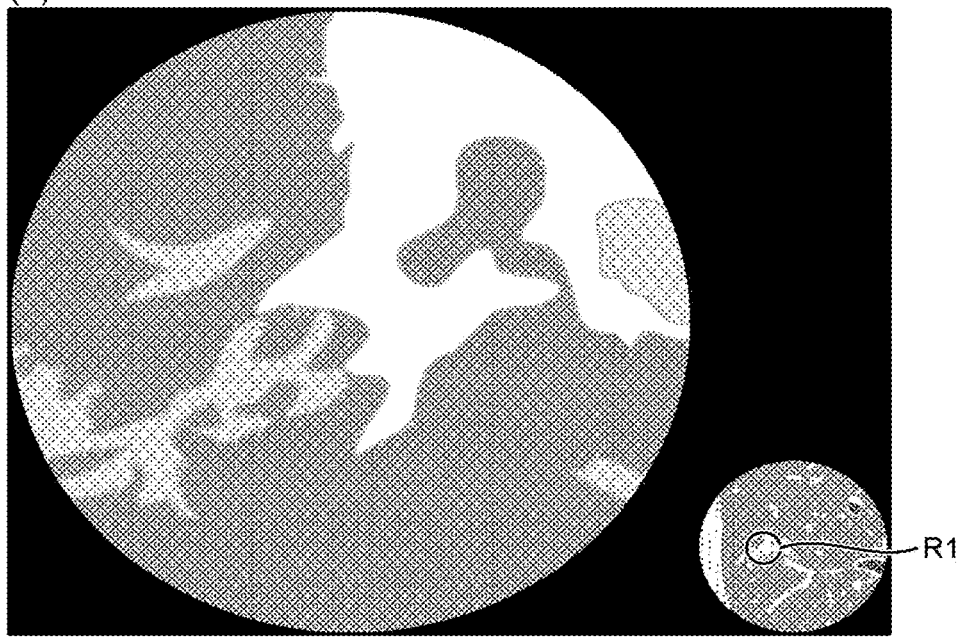

X-RAY CT APPARATUS AND IMAGE DIAGNOSTIC APPARATUS

CROSS-REFERENCE TO RELATED APPLICATIONS

This application is a continuation of PCT international application Ser. No. PCT/JP2014/064032 filed on May 27, 2014 which designates the United States, incorporated herein by reference, and which claims the benefit of priority from Japanese Patent Application No. 2013-111239, filed on May 27, 2013, the entire contents of which are incorporated herein by reference. The entire contents of the prior Japanese Patent Application No. 2014-109537, filed on May 27, 2014, are also incorporated herein by reference.

FIELD

Embodiments described herein relate generally to an X-ray CT apparatus and an image diagnostic apparatus.

BACKGROUND

Conventionally, X-ray computed tomography (CT) apparatus collect projection data by irradiating a subject with X-rays and detecting the X-rays that have passed through the subject, and reconstruct an image from the collected projection data. In recent X-ray CT apparatus, the matrix size of image data to be reconstructed is generally, "512×512". In such a case, for example, if the diameter of the field of view (FOV), which is an imaging region, is 50 cm (500 mm), the size of a single pixel is "about 1 mm (500/512=0.98 mm). If the diameter of the FOV is "25 cm (250 mm), the size of a single pixel is "about 0.5 mm (250/512=0.49 mm).

In the recent X-ray CT apparatus, the maximum resolution defined by the geometry of the system, such as the focal size and the opening width of a detector, is about "0.35 mm". In other words, to achieve the maximum resolution of "0.35" by the matrix size of "512×512", the FOV will be about 18 cm (0.35×512=179.2 mm). To put it differently, when the FOV is larger than "18 cm", it is difficult to achieve the maximum resolution. Accordingly, to achieve the maximum resolution, zooming reconstruction is performed to reduce the FOV. For example, if the FOV is reconstructed into "10 cm", the size of a single pixel will be "about 0.2 mm (100/512)". Consequently, the maximum resolution can be achieved.

However, in the conventional technology described above, it has sometimes been difficult to observe the entire region to be observed with high resolution.

BRIEF DESCRIPTION OF THE DRAWINGS

FIG. 7A is a schematic diagram for explaining an example of setting a region of interest according to the first embodiment;
FIG. 7B is a schematic diagram for explaining an example of setting a region of interest according to the first embodiment;
FIG. 11 is a flowchart for explaining an example of processing performed by the X-ray CT apparatus according to the first embodiment;
FIG. 14 is a schematic diagram for explaining an example of processing performed by the X-ray CT apparatus according to the second embodiment.

DETAILED DESCRIPTION

According to an embodiment, an X-ray computed tomography (CT) apparatus includes an X-ray tube, a detector, processing circuitry, a display and an input circuitry. The X-ray tube is configured to emit an X-ray. The detector is configured to detect the X-ray emitted from the X-ray tube and having passed through a subject. The processing circuitry is configured to collect projection data, based on detection data detected by the detector. The processing circuitry is configured to generate a reconstructed image, based on the projection data. The display is configured to display a display image based on the reconstructed image. The input circuitry is configured to receive an operation to rotate a first display image based on a first reconstructed image generated by the processing circuitry on a display screen of the display, and specify a certain region on a second display image whose axis is in a direction different from a slice direction. The processing circuitry is configured to generate a second reconstructed image based on the projection data so as to have higher resolution than that of the first display image, for the certain region.

Embodiments of an X-ray CT apparatus and an image diagnostic apparatus will now be described in detail below with reference to the accompanying drawings. In the following, an X-ray CT apparatus will be described as an example.

First Embodiment

Figure 1:
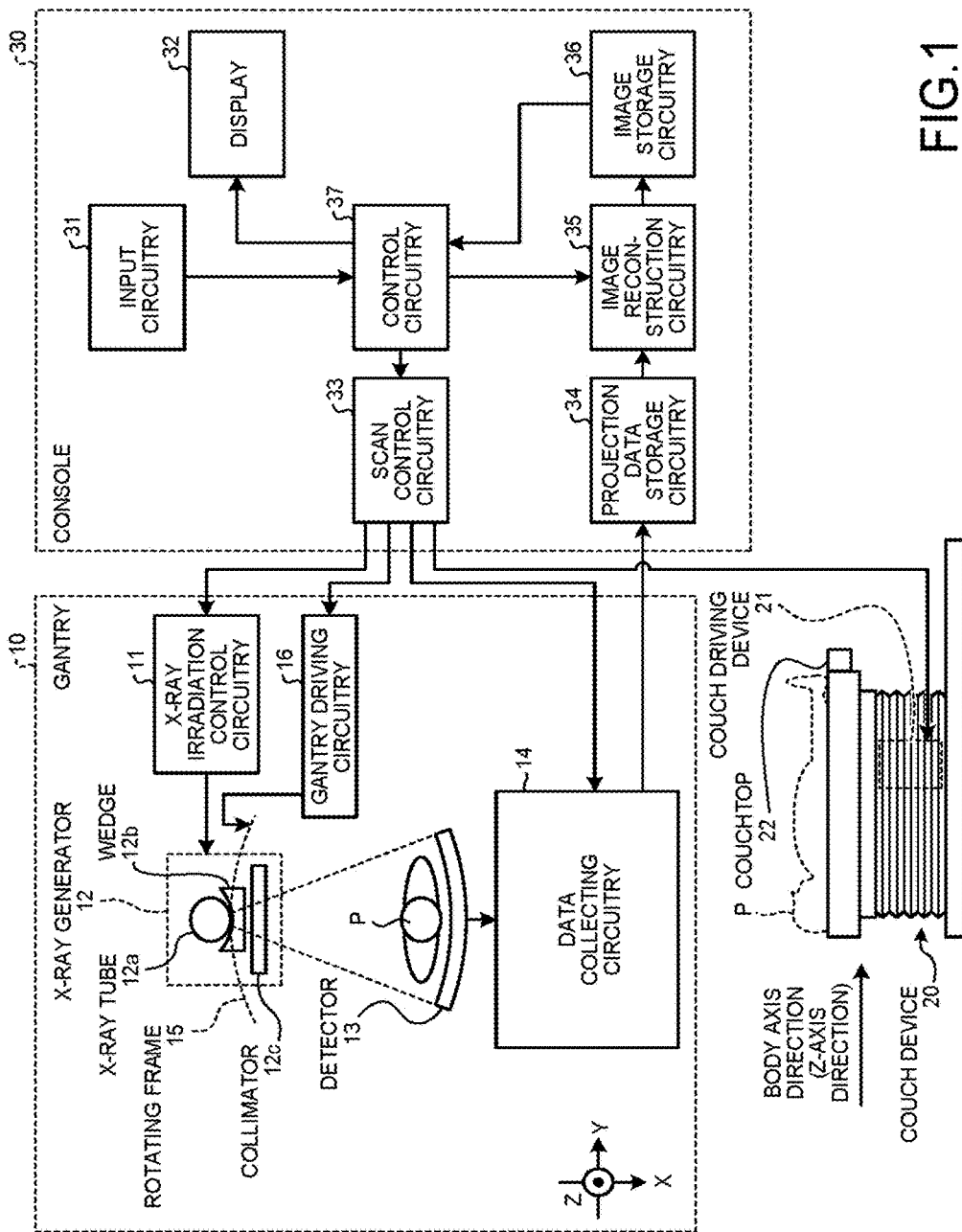
FIG. 1 is a configuration example of an X-ray CT apparatus according to a first embodiment.

A configuration of an X-ray CT apparatus 1 according to a first embodiment will now be described. FIG. 1 is a configuration example of the X-ray CT apparatus 1 according to the first embodiment. As illustrated in FIG. 1, the X-ray CT apparatus 1 according to the first embodiment includes a gantry 10, a couch device 20, and a console 30.

The gantry 10 is a device that detects X-rays emitted to a subject P and having passed through the subject P, and outputs to the console 30. The gantry 10 includes an X-ray irradiation control circuitry 11, an X-ray generator 12, a detector 13, a data collecting circuitry 14, a rotating frame 15, and a gantry driving circuitry 16.

The rotating frame 15 supports the X-ray generation device 12 and the detector 13 facing each other interposing the subject P therebetween. The rotating frame 15 is an annular frame that rotates around the subject P in a circular orbit at a high speed by the gantry driving circuitry 16, which will be described below.

The X-ray generator 12 is a device that generates X-rays and irradiates the subject P with the generated X-rays. The X-ray generator 12 includes an X-ray tube 12a, a wedge 12b, and a collimator 12c.

The X-ray tube 12a is a vacuum tube that irradiates the subject P with X-ray beams, by high voltage supplied from the X-ray generator 12, which will be described below. With the rotation of the rotating frame 15, the subject P is irradiated with X-ray beams. The X-ray tube 12a generates X-ray beams that spread over a fan angle and a cone angle.

The wedge 12b is an X-ray filter that adjusts the amount of X-rays exposed from the X-ray tube 12a. More specifically, the wedge 12b is a filter that transmits and attenuates the X-rays exposed from the X-ray tube 12a so that the X-rays emitted to the subject P from the X-ray tube 12a are distributed in a predetermined manner. For example, the wedge 12b is a filter made by processing aluminum to have a predetermined target angle and a predetermined thickness. The wedge is also referred to as a wedge filter and a bow-tie filter.

The collimator 12c is a slit that narrows down the irradiation range of the X-rays, whose amount is adjusted by the wedge 12b, by the control of the X-ray irradiation control circuitry 11, which will be described below.

The X-ray irradiation control circuitry 11 is a device that supplies high voltage to the X-ray tube 12a, as a high-voltage generation circuitry. The X-ray tube 12a generates X-rays by using the high voltage supplied from the X-ray irradiation control circuitry 11. The X-ray irradiation control circuitry 11 adjusts the amount of X-rays emitted to the subject P, by adjusting the tube voltage and tube current supplied to the X-ray tube 12a.

The X-ray irradiation control circuitry 11 switches the wedge 12b. The X-ray irradiation control circuitry 11 also adjusts the irradiation range (fan angle and cone angle) of X-rays, by adjusting the opening angle of the collimator 12c.

In the present embodiment, an operator may manually switch a plurality of types of wedges.

The gantry driving circuitry 16 rotates the X-ray generator 12 and the detector 13 in the circular orbit around the subject P, by rotating and driving the rotating frame 15.

The detector 13 is a two-dimensional array-type detector (plane detector) that detects the X-rays emitted from the X-ray tube 12a and having passed through the subject P. A plurality of rows of detection element strings, which are X-ray detection elements arranged in a plurality of channels, are disposed along the body axis direction (Z-axis direction in FIG. 1) of the subject P. More specifically, the detector 13 according to the first embodiment includes X-ray detection elements that are arranged in multiple rows, such as 320 rows, along the body axis direction of the subject P. The detector 13, for example, is capable of detecting X-rays that have passed through the subject P in a wide range, such as a range including the lungs and heart of the subject P.

The data collecting circuitry 14 generates projection data using the X-rays detected by the detector 13, and transmits the generated projection data to a projection data storage circuitry 34 in the console 30.

The couch device 20 is a device on which the subject P is to be laid, and as illustrated in FIG. 1, includes a couch driving circuitry 21 and a couchtop 22. The couch driving circuitry 21 moves the couchtop 22 in the Z-axis direction, and moves the subject P into the rotating frame 15. The couchtop 22 is a plate on which the subject P is to be laid.

For example, the gantry 10 performs a helical scan in which the subject P is scanned in a spiral form, by moving the couchtop 22 and rotating the rotating frame 15. Alternatively, the gantry 10 performs a conventional scan in which the subject P is scanned in a circular orbit by rotating the rotating frame 15, after moving the couchtop 22 and fixing the position of the subject P. Alternatively, the gantry 10 performs a step-and-shoot method in which the position of the couchtop 22 is moved at a regular interval and a conventional scan is performed in a plurality of scanning areas.

The console 30 is a device that receives an operation of the X-ray CT apparatus 1 by the operator, and reconstructs X-ray CT image data by using the projection data collected by the gantry 10. The console 30, as illustrated in FIG. 1, includes an input circuitry 31, a display 32, a scan control circuitry 33, the projection data storage circuitry 34, an image reconstruction circuitry 35, an image storage circuitry 36, and a control circuitry 37.

The input circuitry 31 includes a mouse, a keyboard, or the like used to input various instructions and various settings by the operator of the X-ray CT apparatus. The input circuitry 31 transmits the instructions and setting information received from the operator, to the control circuitry 37. For example, the input circuitry 31 receives imaging conditions of X-ray CT image data, reconstruction conditions when the X-ray CT image data is reconstructed, image processing conditions relative to the X-ray CT image data, and the like from the operator.

The display 32 is a monitor referred to by the operator. The display 32 displays X-ray CT image data for the operator and displays a graphical user interface (GUI) to receive various instructions, various settings, and the like, from the operator via the input circuitry 31, under the control of the control circuitry 37.

The scan control circuitry 33 controls collection processing of projection data in the gantry 10, by controlling the operations of the X-ray irradiation control circuitry 11, the gantry driving circuitry 16, the data collecting circuitry 14, and the couch driving circuitry 21, under the control of the control circuitry 37, which will be described below.

The projection data storage circuitry 34 stores therein projection data generated by the data collecting circuitry 14. In other words, the projection data storage circuitry 34 stores therein projection data to reconstruct X-ray CT image data.

The image reconstruction circuitry 35 reconstructs X-ray CT image data (reconstructed image) by using the projection data stored in the projection data storage circuitry 34. There are various reconstruction methods, and for example, one of them is back projection processing. The back projection processing may be performed, for example, by a filtered back projection (FBP) method. The image reconstruction circuitry 35 generates a CT image (display image) by performing various types of image processing on the X-ray CT image data (reconstructed image). The image reconstruction circuitry 35 stores the reconstructed X-ray CT image data and the CT image generated by performing various types of image processing, in the image storage circuitry 36. The image storage circuitry 36 stores therein the X-ray CT image data and the CT image generated by the image reconstruction circuitry 35.

The control circuitry 37 controls the entire X-ray CT apparatus by controlling the operations of the gantry 10, the couch device 20, and the console 30. More specifically, the control circuitry 37 controls the CT scan performed in the gantry 10, by controlling the scan control circuitry 33. The control circuitry 37 also controls the image reconstruction processing and the image generation processing at the console 30, by controlling the image reconstruction circuitry 35. The control circuitry 37 also controls the display 32 to display various pieces of image data stored in the image storage circuitry 36 on the display 32.

The overall configuration of the X-ray CT apparatus according to the first embodiment has been described above. With this configuration, the X-ray CT apparatus according to the first embodiment enables the observer to easily observe the entire region to be observed with high resolution. In a conventional technology, it has sometimes been difficult to observe the entire region to be observed with high resolution. Hereinafter, this will be described. Traditionally, to observe medical images, for example, a wide range image including a region of interest is first observed. The region of interest is then selected, and an image in which the region of interest is enlarged is observed.

Figure 2A:
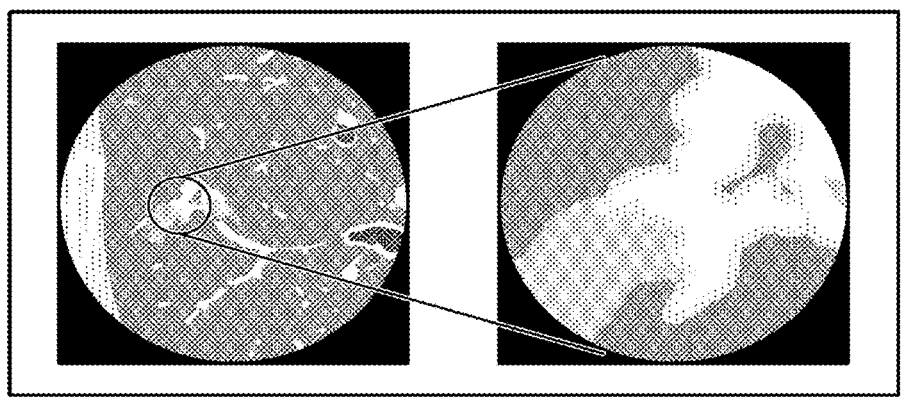
FIG. 2A is a schematic diagram of an example of a medical image in standard resolution according to the first embodiment.
Figure 2B:
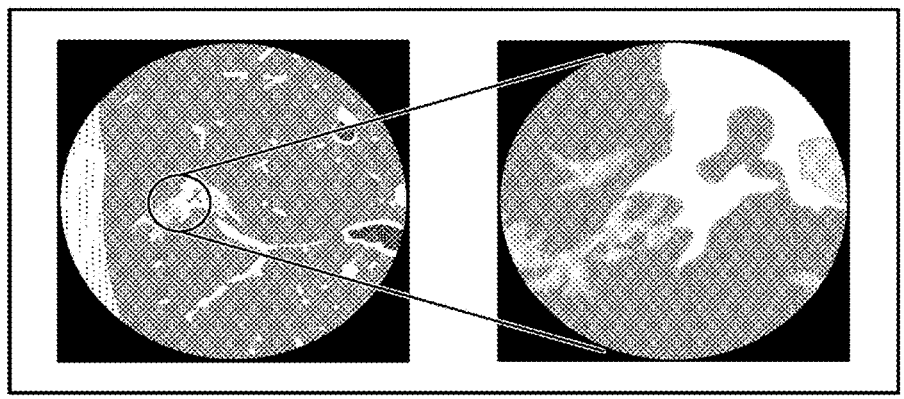
FIG. 2B is a schematic diagram of an example of a medical image in high resolution according to the first embodiment.

FIG. 2A is a schematic diagram of an example of a medical image in standard resolution according to the first embodiment. FIG. 2B is a schematic diagram of an example of a medical image in high resolution according to the first embodiment. In FIG. 2A and FIG. 2B, the left side is a CT image including a wide range of areas, and the right side is a CT image of an area selected from the wide-range CT image at the left. For example, as illustrated in FIG. 2A, in the CT image in standard resolution, when a certain region is selected from the wide-range CT image, the image is blurred and cannot be observed properly. On the other hand, as illustrated in FIG. 2B, in the CT image in high resolution, even if a certain region is selected from the wide-range CT image, it is possible to be observed properly.

Figure 3A:
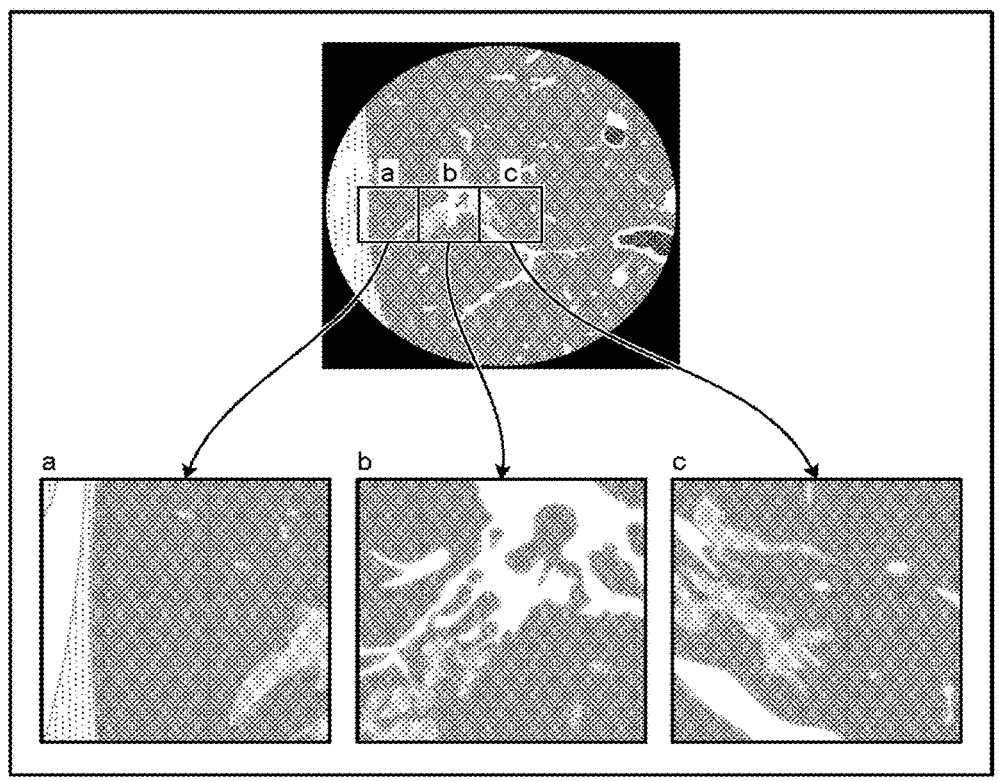
FIG. 3A is a schematic diagram for explaining an example of zooming reconstruction according to the first embodiment.

As described above, in the X-ray CT apparatus, image data with a matrix size of "512×512" is generally handled. Accordingly, to obtain a CT image in high resolution, zooming reconstruction is performed to reduce the FOV. In other words, in a conventional technology, because the matrix size of image data is small, there is a trade-off between selecting either the low resolution data in a wide region or the high-resolution data in a limited region. FIG. 3A is a schematic diagram for explaining an example of zooming reconstruction according to the first embodiment.

For example, in a conventional technology, an observer first observes the wide range of areas with standard resolution (for example, the FOV of 500 mm and the matrix size of 512×512) as illustrated in the upper diagram in FIG. 3A. Then, the observer selects regions a, b, and c, as regions of interest to be observed in more detail. In other words, the observer can observe a CT image in high resolution for each region, by executing zooming reconstruction to reduce the FOV, while keeping the matrix size.

In recent years, with a development of an area detector CT (ADCT), direct coronal imaging has been possible. For example, a technology of imaging 16-cm area in the slice direction by a single rotation of the X-ray tube is also known. In such a case, an area of 16 cm on the coronal plane can be observed by a single scan, and for example, in orthopedic surgery, expectations are rising to observe an affected area in detail by moving image. However, if a long and slender portion such as an arm or a leg is affected, the entire region does not fit in the slice direction. To scan an object to be imaged including the affected area in a single scan, the scan is executed by arranging the object to be imaged so that the longitudinal direction is substantially in parallel to the direction perpendicular to the slice direction, with the FOV being "40 cm" or "50 cm". Accordingly, in such a case, the resolution is reduced, and it is difficult to observe the entire region to be observed with high resolution.

Figure 3B:
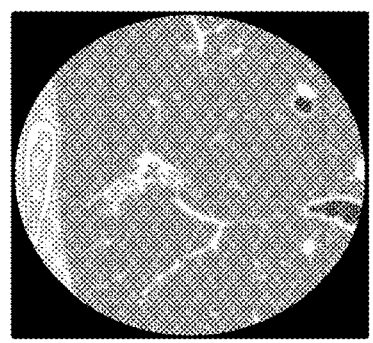
FIG. 3B is a schematic diagram for explaining an example of improving the resolution by changing the matrix size according to the first embodiment.

If the FOV is large and it is difficult to achieve the maximum resolution defined by the geometry of the system and the like, there is a method of increasing the resolution by increasing the matrix size. FIG. 3B is a schematic diagram for explaining an example of improving resolution by changing the matrix size according to the first embodiment. FIG. 3B illustrates a CT image when the matrix size is increased (for example, 512×512 is changed to 4096×4096). In FIG. 3B, the size of the reconstructed CT image is reduced so as to be the same as that of FIG. 3A, and the physical pixel size is reduced to one eighth. For example, when the matrix size is increased, as illustrated in FIG. 3B, the resolution of the entire CT image is improved. However, even if the matrix size is simply increased, it is not possible to achieve the resolution higher than the maximum resolution defined by the geometry of the system and the like, and the data size is also increased with the increase of the matrix size. For example, if 512×512 is changed to 4096×4096, the data size is increased by 64 times (=8×8).

Accordingly, when the reconstructed image is to be stored or processed, or when the image data is to be transferred via a network, a heavy load is imposed. Consequently, the matrix size cannot be easily increased, and it is difficult to observe the entire region to be observed with higher resolution.

In the X-ray CT apparatus 1 and a medical image diagnostic apparatus according to the present embodiment, it is possible to observe the entire region to be observed with higher resolution, regardless of the arrangement of the portion of interest in image data (for example, projection data), because the control circuitry 37, which will be described in detail below, performs control so that only the specified region is reconstructed with high resolution.

Figure 4:
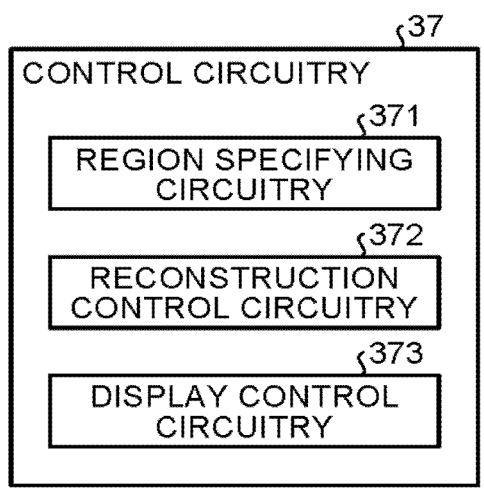
FIG. 4 is a schematic diagram of an example of a configuration of a control circuitry according to the first embodiment.

FIG. 4 is a schematic diagram of an example of a configuration of the control circuitry 37 according to the first embodiment. For example, the control circuitry 37, as illustrated in FIG. 4, includes a region specifying circuitry 371, a reconstruction control circuitry 372, and a display control circuitry 373. Here, in the X-ray CT apparatus 1 according to the first embodiment, scanning of an imaging portion of the subject P is performed, and the projection data is collected. In the X-ray CT apparatus 1, the image reconstruction circuitry 35 generates a CT image by reconstructing the X-ray CT image data in standard resolution (for example, the matrix size of 512×512 and the FOV of 50 cm) by using the collected projection data. The display control circuitry 373 then displays the generated CT image on the display 32.

Figure 5:
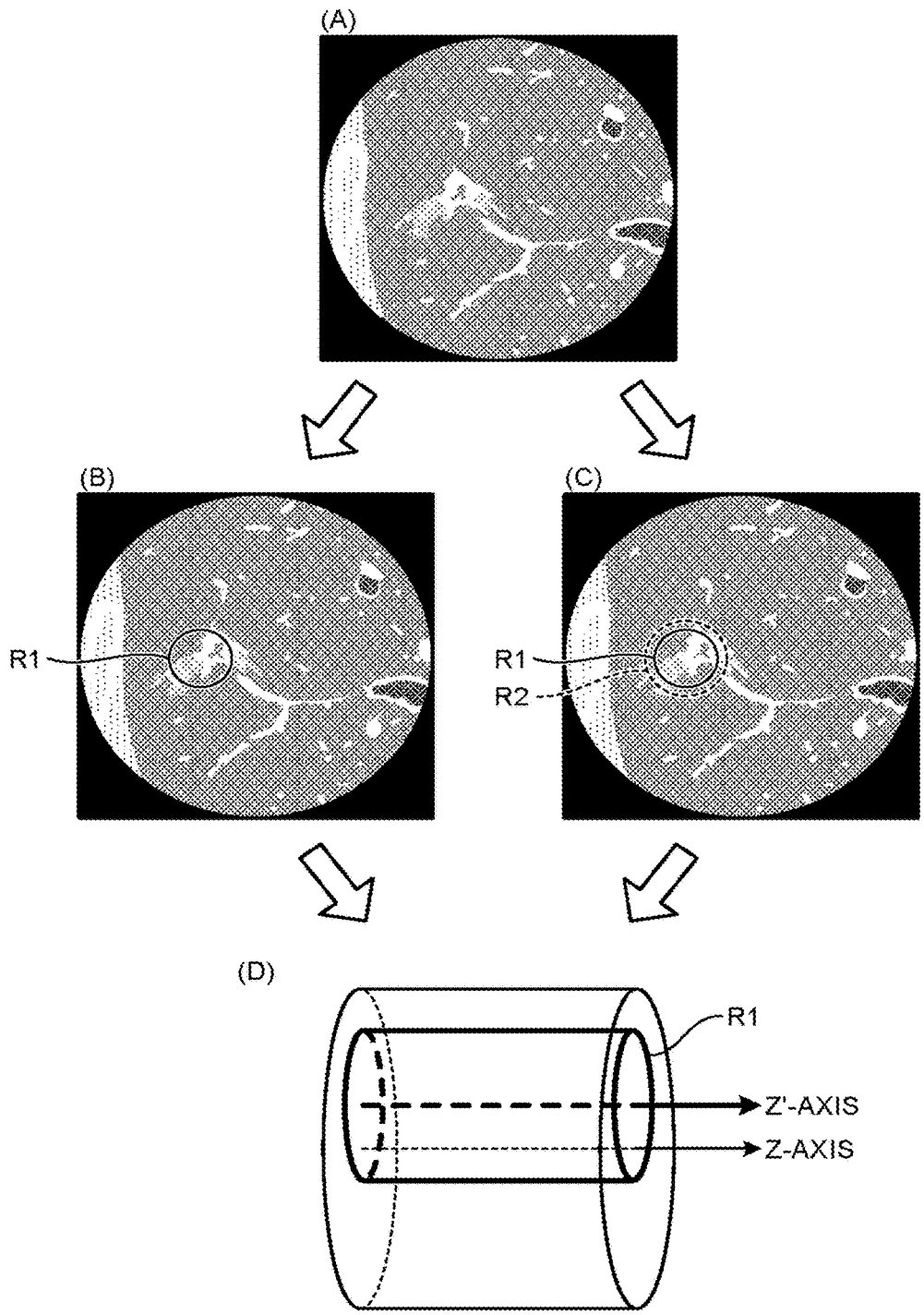
FIG. 5 is a schematic diagram for explaining an example of processing performed by a region specifying circuitry according to the first embodiment.

The observer then refers to the CT image displayed on the display 32, and selects a region of interest that the observer desires to observe in high resolution, via the input circuitry 31. In other words, the input circuitry 31 receives a specifying operation of a certain region in a first CT image (for example, a standard-resolution image). The region specifying circuitry 371 specifies a region in the projection data corresponding to the specified region via the input circuitry 31. FIG. 5 is a schematic diagram for explaining an example of processing performed by the region specifying circuitry 371 according to the first embodiment. (A) in FIG. 5 illustrates a CT image in standard resolution displayed on the display 32. (B) and (C) in FIG. 5 illustrate CT images in which regions of interest are specified by the operator. (D) in FIG. 5 illustrates an example of specifying a region of interest by the region specifying circuitry 371.

For example, the display control circuitry 373, as illustrated in (A) in FIG. 5, when the CT image in standard resolution is displayed on the display 32, the input circuitry 31, as illustrated in (B) in FIG. 5, receives a specifying operation of a region of interest R1 by the observer. The region specifying circuitry 371 then specifies the position of the region of interest R1 received via the input circuitry 31 in the projection data. In other words, the region specifying circuitry 371, as illustrated in (D) in FIG. 5, specifies a three-dimensional region of the region of interest R1 around the Z'-axis, which is in parallel to the Z-axis. Z-axis is the center axis of the scanned projection data in the slice direction.

For example, the region specifying circuitry 371 specifies the three-dimensional region of the region of interest R1, based on coordinate information of the projection data. Here, the input circuitry 31, as illustrated in (C) in FIG. 5, can further receive a specifying operation of a peripheral region R2, outside the region of interest R1. In such a case, the region specifying circuitry 371 specifies the position of the region of interest R1 as well as the position of the peripheral region R2. In FIG. 5, the region of interest R1 and the peripheral region R2 are specified on the two-dimensional CT image. However, embodiments are not limited thereto, and the region of interest R1 and the peripheral region R2 may be specified on a three-dimensional CT image. In such a case, for example, the display control circuitry 373 may specify the region of interest R1 and the peripheral region R2 on the three-dimensional CT image displayed as illustrated in (D) in FIG. 5.

The sizes of the region of interest R1 and the peripheral region R2 may be arbitrarily set by the observer. In other words, the input circuitry 31 can receive independent specifying operations of the region of interest R1 and the peripheral region R2, respectively. The peripheral region R2 may be automatically set, when the specifying operation of the region of interest R1 is executed. For example, the peripheral region R2 may be set as a region having a diameter larger than that of the region of interest R1 by a predetermined value. In FIG. 5, the region of interest R1 and the peripheral region R2 are specified in circles (cylinders). However, embodiments are not limited thereto, and the region of interest R1 and the peripheral region R2 may be specified in squares (quadrangular prisms).

Figure 6:
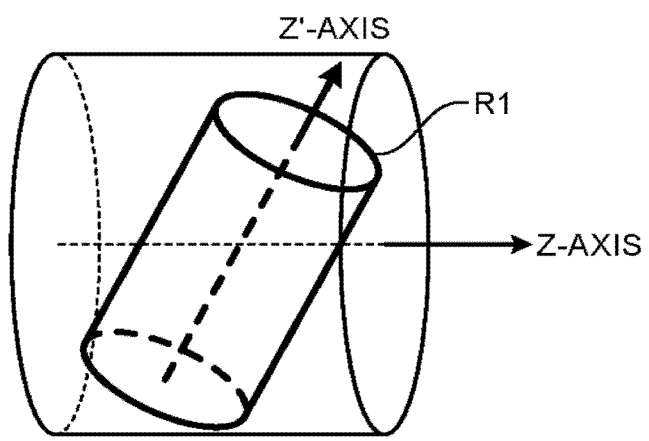
FIG. 6 is a schematic diagram of an example of specifying a region of interest by the region specifying circuitry according to the first embodiment.

Here, the region specifying circuitry 371 may also specify a position of the region of interest R1 in which the Z'-axis is set not parallel to the Z-axis (so as to have a certain angle relative to the Z-axis), in addition to the specifying operation of the region in which the Z'-axis is parallel to the Z-axis. In other word, the input circuitry 31 receives a specifying operation of a region whose axis is in a direction parallel to the slice direction of three-dimensional image data, or a region whose axis is in a direction different from the slice direction (direction having a certain angle relative to the slice direction) of three dimensional image data, as the certain region. FIG. 6 is a schematic diagram of an example of specifying a region of interest by the region specifying circuitry 371 according to the first embodiment.

For example, the region specifying circuitry 371, as illustrated in FIG. 6, specifies the position of the region of interest R1 having a certain angle relative to the Z-axis of the projection data, in the projection data. In such a case, for example, the display control circuitry 373 displays a three-dimensional CT image as illustrated in FIG. 6, on the display 32. The input circuitry 31, as illustrated in FIG. 6, then receives a specifying operation of the region of interest R1 with reference to the Z'-axis having a certain angle relative to the Z-axis.

Alternatively, the display control circuitry 373 displays multi-planar reconstruction (MPR) images in three orthogonal planes on the display 32, and the input circuitry 31 receives the setting of the oblique plane. Consequently, the region of interest R1 is selected, and as illustrated in FIG. 6, the region specifying circuitry 371 specifies the position of the region of interest R1 having a certain angle relative to the Z-axis of the projection data, in the projection data.

Here, the setting of a region whose axis is in a direction different from the slice direction will be described with reference to FIG. 7A and FIG. 7B. FIG. 7A and FIG. 7B are schematic diagrams for explaining examples of setting a region of interest according to the first embodiment. FIG. 7A illustrates the setting using MPR images, and FIG. 7B illustrates the setting using volume rendering images. In FIG. 7A, (A) illustrates MPR images with respect to the original axis, and (B) illustrates MPR images with respect to the axis after being set. In both (A) and (B) in FIG. 7A, the upper left indicates the axial plane, the upper right indicates the sagittal plane, and the lower left indicates the coronal plane.

To set a region whose axis is in a direction different from the slice direction by using MPR images, the display 32 first displays MPR images in three orthogonal planes with respect to the original axis, as illustrated in (A) in FIG. 7A. For example, in the MPR images with respect to the original axis, as illustrated in (A) in FIG. 7A, the Z-axis (axis in the slice direction) in the axial plane is in a direction perpendicular to the diagram. In the MPR images with respect to the original axis, for example, the axial plane is illustrated in a circle whose diameter is the FOV of the standard-resolution region, and the sagittal plane is illustrated in a rectangle in which the length is the FOV of the standard-resolution region and the width is a display region of the standard-resolution region in the Z-axis direction (Z-FOV). The coronal plane is illustrated in a rectangle in which the length is the Z-FOV and the width is the FOV.

The operator, while observing the MPR images in standard resolution such as these, sets the region to be observed with high resolution. Here, (A) in FIG. 7A illustrates a region to be observed with high resolution included in the standard-resolution region. In other words, the operator, while observing the MPR images in standard resolution, performs the following operation to set the region indicated in a cylinder. The cylinder in (A) in FIG. 7A means that the portion to be observed is included therein, and in practice, the cylinder (region of interest R1) is not defined at this point. In the MPR images with respect to the original axis as illustrated in (A) in FIG. 7A, data with a matrix size of 512×512 is generally used. However, if they are used for setting a high-resolution region, data with a smaller matrix size may be used.

For example, the operator, while observing the MPR images illustrated in (A) in FIG. 7A, operates the input circuitry 31 and rotates the displayed image, such that the circle including the portion to be observed in the axial plane becomes the smallest. As an example, the operator operates the input circuitry 31, and as illustrated in (B) in FIG. 7A, rotates the displayed image until the cylinder indicating the high-resolution region in the axial plane is in a direction viewed from the axial direction. The operator, when the cylinder in the axial plane is in a direction viewed from the axial direction, sets it as the Z'-axis. In other words, in the MPR images with respect to the set axis, as illustrated in (B) in FIG. 7A, the Z'-axis in the axial plane is indicated in a direction perpendicular to the diagram, and has a certain angle relative to the original Z-axis.

When the circle in the axial plane is set in this manner, the operator, for example, while observing the coronal plane, sets the display region in the Z'-axis direction (Z'-FOV). Consequently, the region of interest R1 to be observed in high resolution is set. At this time, in the MPR images with respect to the set axis, as illustrated in (B) in FIG. 7A, the axial plane is illustrated in a circle whose diameter is the FOV of the high-resolution region, and the sagittal plane is illustrated in a rectangle in which the length is the FOV of the high-resolution region and the width is the Z'-FOV of the high-resolution region. The coronal plane is illustrated in a rectangle in which the length is the Z'-FOV and the width is the FOV of the high-resolution region. In (B) in FIG. 7A, the X'-axis and the Y'-axis are each included in the plane perpendicular to the Z'-axis, and are orthogonal to each other. However, it is not necessary to define the X'-axis and the Y'-axis to set the region of interest R1. In other words, by rotating and adjusting the image in the direction illustrated in (B) in FIG. 7A, the direction of the Z'-axis can be set, and the cylinder can be defined by referring to it.

As described above, in the X-ray CT apparatus 1 according to the first embodiment, the region of interest R1 whose axis is in a direction different from the slice direction is set by using the MPR image. In other words, the input circuitry 31 receives an operation to rotate a first display image based on a first reconstructed image generated by the image reconstruction circuitry 35 on the display screen of the display 32, and specify a certain region on a second display image whose axis is in a direction different from the slice direction. In the example described above, the display images are MPR images. However, embodiments are not limited thereto, and for example, volume rendering images may be used for the setting.

For example, as illustrated in (A) in FIG. 7B, the display 32 displays a volume rendering image with respect to the original axis in the FOV of the standard-resolution region. The operator operates the input circuitry 31, and as illustrated in (B) in FIG. 7B, sets the circle indicating the FOV of the high-resolution region, by setting the direction of the Z'-axis, while rotating the image so that the circle including the portion to be observed becomes the smallest. The operator then operates the input circuitry 31, and as illustrated in (C) in FIG. 7B, further rotates the image and sets the display region in the Z'-axis direction (Z'-FOV). However, the display image is not limited to the ones described above, and for example, an MIP image, whose normal direction relative to the display screen is in the line of sight, may be used.

In the example described above, the FOV of the high-resolution region (for example, the circle in the axial plane) is set before setting the display region in the Z'-axis direction (Z'-FOV). However, for example, if the region including the portion to be observed in the Z'-axis direction is from one end to the other end of the standard-resolution region, the Z'-FOV may be set automatically. In such a case, the input circuitry 31, when a certain region in a two-dimensional manner is specified in the horizontal direction relative to the display screen on the second display image, sets a three-dimensional region capable of generating a second reconstructed image that has higher resolution than that of the first display image on the projection data, based on the certain region.

The example of setting the region of interest R1 described above is merely an example, and embodiments are not limited thereto. For example, in the example described above, a cylinder is used to set the region of interest R1. However, a prism may be used to set the region of interest instead. In such a case, the FOV of the high-resolution region illustrated in FIG. 7A and FIG. 7B is a quadrangle.

As described above, the region specifying circuitry 371 specifies the position of the region of interest R1 having a certain angle relative to the Z-axis of the projection data, in the projection data. Similarly to the above, the region specifying circuitry 371 also specifies a three-dimensional region of the region of interest R1, based on the coordinate information of the projection data. Here, the region specifying circuitry 371 calculates information such as the size of cross-section perpendicular to the Z'-axis, the matrix size, the length in the Z'-axis direction, and the positional relation (for example, direction and distance) between the Z'-axis and the Z-axis, of the region of interest R1 or the peripheral region R2, from the coordinate information of the projection data. The region specifying circuitry 371 then stores the calculated information as information to specify various regions.

Returning to FIG. 4, the reconstruction control circuitry 372 generates a second medical image that has higher resolution than that of a first medical image, from the image data used for generating the first medical image, for the certain region received by the input circuitry 31. More specifically, the reconstruction control circuitry 372 controls the image reconstruction circuitry 35 so as to generate the second reconstructed image based on the projection data so as to have higher resolution than that of the first display image, for the set certain region. More specifically, the reconstruction control circuitry 372 generates a CT image by reconstructing a high-resolution reconstructed image by using the projection data from which the standard-resolution CT image is generated, for the region of interest or the peripheral region including the region of interest specified by the region specifying circuitry 371.

Figure 8A:
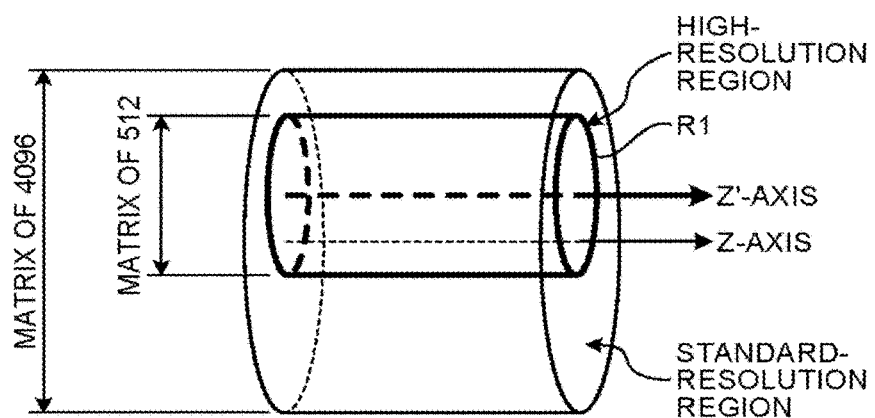
FIG. 8A is a schematic diagram for explaining an example of processing performed by a reconstruction control circuitry according to the first embodiment.
Figure 8B:
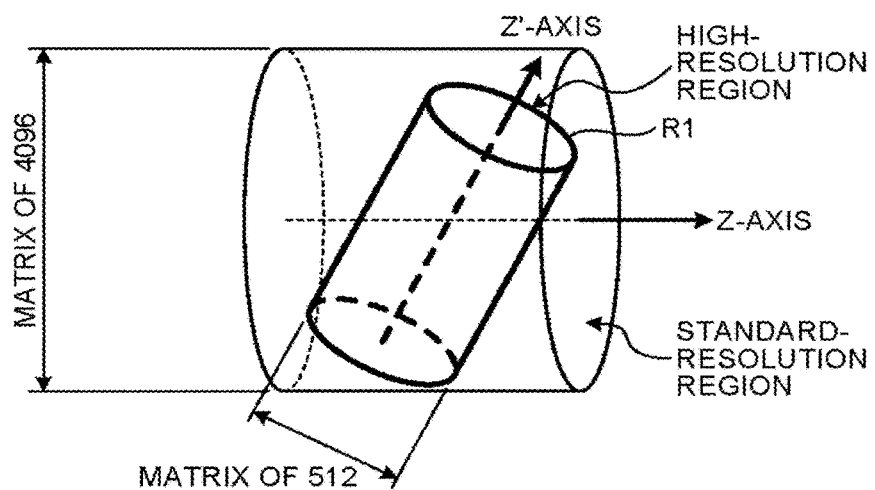
FIG. 8B is a schematic diagram for explaining an example of processing performed by the reconstruction control circuitry according to the first embodiment.

FIG. 8A and FIG. 8B are schematic diagrams for explaining an example of processing performed by the reconstruction control circuitry 372 according to the first embodiment. FIG. 8A illustrates when the Z'-axis of the region of interest is parallel to the Z-axis. FIG. 8B illustrates when the Z'-axis of the region of interest has a certain angle relative to the Z-axis.

For example, if the Z'-axis of the region of interest is parallel to the Z-axis, as illustrated in FIG. 8A, similarly to the conventional zooming reconstruction, the reconstruction control circuitry 372 controls the image reconstruction circuitry 35 so that the region of interest R1 is reconstructed into a high-resolution region in a matrix of 512.

If the Z'-axis of the region of interest has a certain angle relative to the Z-axis, for example, the reconstruction control circuitry 372, as illustrated in FIG. 8B, temporarily sets a region to be reconstructed so as to include the entire region of interest R1. Here, for example, as illustrated in FIG. 8B, the reconstruction control circuitry 372 obtains high-resolution data of a region corresponding to the region of interest R1, by extracting image data of the region of interest R1 equivalent to a matrix of 512, from the data of the region temporarily reconstructed to a matrix of 4096.

There are times when the positional relation between the voxels of the region of interest R1 to be extracted and the voxels of the entire region to be temporarily reconstructed does not correspond with each other. Accordingly, the reconstruction control circuitry 372 extracts voxel data of the region of interest R1 by complementing the region of interest R1 to be extracted with voxel data of the entire region to be temporarily reconstructed.

Figure 9A:
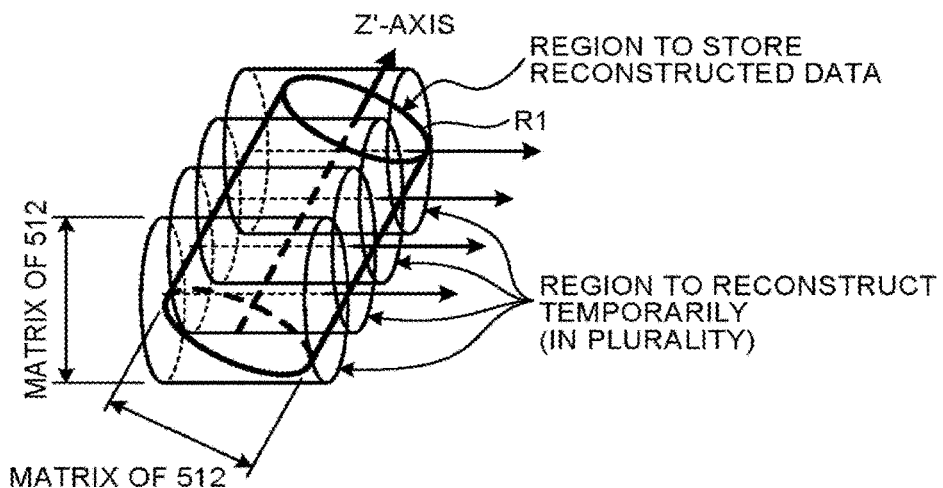
FIG. 9A is a schematic diagram for explaining an example of control performed by the reconstruction control circuitry according to the first embodiment.
Figure 9B:
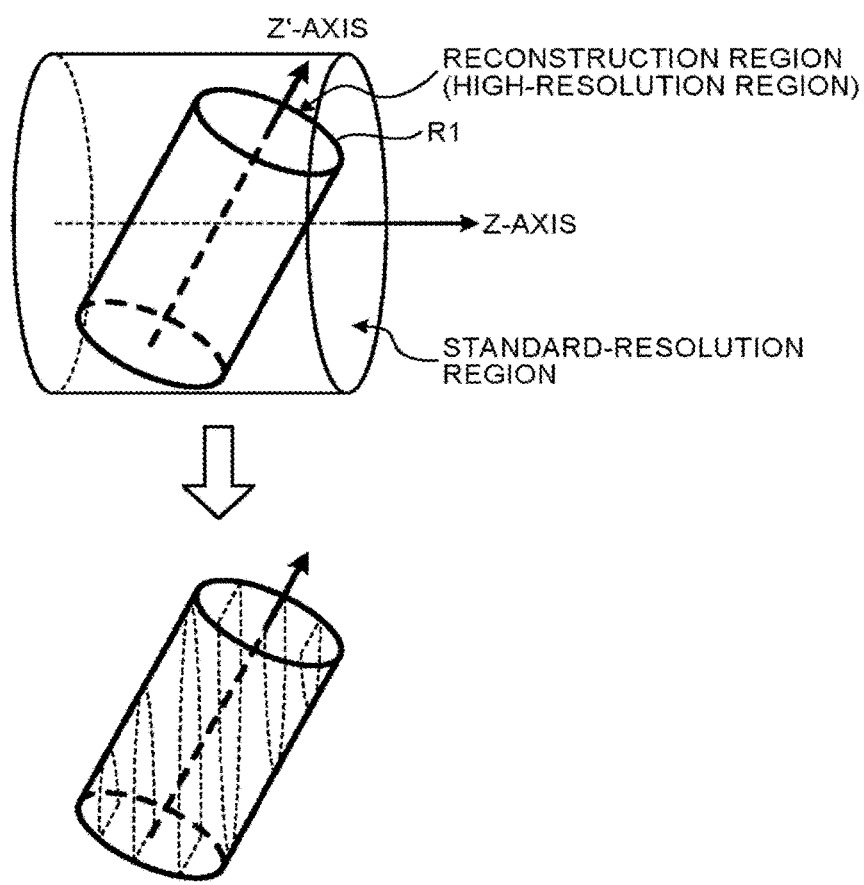
FIG. 9B is a schematic diagram for explaining an example of control performed by the reconstruction control circuitry according to the first embodiment.

As described above, when the Z'-axis of the region of interest is parallel to the Z-axis, and also when the Z'-axis of the region of interest has a certain angle relative to the Z-axis, the reconstruction control circuitry 372 can reconstruct the high-resolution reconstructed image of the region of interest R1, and generate a CT image. Here, the reconstruction control circuitry 372 according to the present embodiment, when the Z'-axis of the region of interest has a certain angle relative to the Z-axis, can reconstruct the high-resolution reconstructed image of the region of interest R1 and generate a CT image by using various methods other than the method described above. FIG. 9A and FIG. 9B are schematic diagrams for explaining examples of control performed by the reconstruction control circuitry 372 according to the first embodiment.

For example, as illustrated in FIG. 9A, when the input circuitry 31 receives a specifying operation on the region whose axis is in a direction having a certain angle relative to the slice direction of the three-dimensional image data, the reconstruction control circuitry 372 sets a plurality of sub-regions in the direction parallel to the slice direction so as to include the region received in the specifying operation. The reconstruction control circuitry 372 then generates the second medical image corresponding to the region received in the specifying operation from the image data of the set sub-regions.

In other words, as illustrated in FIG. 9A, the reconstruction control circuitry 372 sets four regions with a matrix size of 512 so as to include the region of interest R1. The reconstruction control circuitry 372 then temporarily reconstructs the four set regions, and obtains high-resolution data of the region corresponding to the region of interest R1. Here, the temporarily reconstructed four regions have portions that are partially overlapped with each other. Consequently, the reconstruction control circuitry 372, for the portions of the four regions that are partially overlapped with each other, executes processing such as average processing, addition of a predetermined weight based on the distance from the middle plane of the overlapped regions, or selection of a value from one of the overlapping regions. In such a case, there are also times when the positional relation between the voxels of the region of interest R1 to be extracted and the voxels of the entire region to be temporarily reconstructed does not correspond with each other. Accordingly, the reconstruction control circuitry 372 extracts voxel data of the region of interest R1 by complementing the region of interest R1 to be extracted with voxel data of the four regions to be temporarily reconstructed. By using the method illustrated in FIG. 9A, the matrix size to be handled can be kept fixed to 512×512. As a result, it is possible to reduce processing load.

For example, as illustrated in FIG. 9B, the reconstruction control circuitry 372 can directly reconstruct image data of the region of interest R1. For example, as illustrated in FIG. 9B, the reconstruction control circuitry 372, in the region of interest R1, calculates each voxel value for each plane, by performing back projection processing relative to the voxels on the plane (plane illustrated in dotted lines in the lower diagram in FIG. 9B) perpendicular to the Z-axis. The reconstruction control circuitry 372 then converts the calculated voxel value of each plane into reconstructed data of a matrix of 512 on the basis of the Z'-axis. To reconstruct the cone beam used in the ADCT, a back projection processing is performed on the voxels included in the region of interest R1, instead of the plane in the region of interest R1, and converts the value of each voxel into the reconstructed data of a matrix of 512 on the basis of the Z'-axis.

Figure 10A:
FIG. 10A is a schematic diagram of an example of an image displayed by the control of a display control circuitry according to the first embodiment.
Figure 10B:
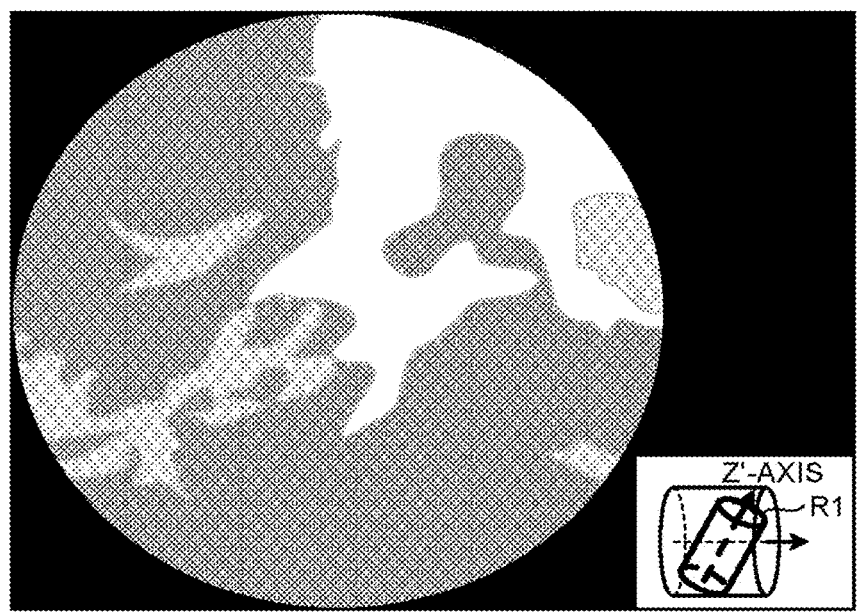
FIG. 10B is a schematic diagram of an example of an image displayed by the control of the display control circuitry according to the first embodiment.

Returning to FIG. 4, the display control circuitry 373 performs control so that the second medical image generated by the reconstruction control circuitry 372 is displayed on the display 32. FIG. 10A and FIG. 10B are schematic diagrams of examples of an image displayed by the control of the display control circuitry 373 according to the first embodiment. FIG. 10A illustrates when the region of interest R1 is specified on a two-dimensional CT image. FIG. 10B illustrates when the region of interest R1 is specified on a three-dimensional CT image.

For example, as illustrated in FIG. 10A, the display control circuitry 373 displays a high-resolution CT image and a reference image indicating the region of interest R1 specified on the entire two-dimensional CT image in standard resolution, on the display 32. Similarly, as illustrated in FIG. 10B, the display control circuitry 373 displays a high-resolution CT image and a reference image indicating the region of interest R1 specified on the entire three-dimensional CT image in standard resolution, on the display 32. Here, the display control circuitry 373 can display the peripheral region R2 in addition to the region of interest R1, on both the two-dimensional reference image and the three-dimensional reference image. In other words, the display control circuitry 373, when the peripheral region is specified in advance, displays the peripheral region R2 outside the region of interest R1.

The display control circuitry 373 can also display the entire CT image in standard resolution, the matrix size of the high-resolution CT image, the Z-axis, and the Z'-axis, simultaneously. Here, the reference images illustrated in FIG. 10A and FIG. 10B may be functioned as graphical user interfaces (GUIs). In other words, a high-resolution CT image of the corresponding region is displayed in the center of the display 32, when the observer operates the input circuitry 31 and moves and rotates the region of interest R1 in the reference image.

Next, with reference to FIG. 11, processing performed by the X-ray CT apparatus according to the first embodiment will be described. FIG. 11 is a flowchart for explaining an example of processing performed by the X-ray CT apparatus according to the first embodiment.

For example, as illustrated in FIG. 11, in the X-ray CT apparatus 1 according to the first embodiment, scanning is executed (step S101), and standard-resolution image data is reconstructed by using projection data and is stored (step S102). The display control circuitry 373 then displays the reconstructed standard-resolution image data on the display (step S103).

The input circuitry 31 then determines whether the display region (for example, the region of interest R1) to display a high-resolution image is specified (step S104). If it is determined that the display region is specified (Yes at step S104), the reconstruction control circuitry 372 controls the image reconstruction circuitry 35 so as to reconstruct the selected region with high resolution (step S105). The display control circuitry 373 then displays the reconstructed high-resolution image data on the display 32 (step S106), and determines whether the display region is changed (step S107).

If the display region is changed (Yes at step S107), the display control circuitry 373 determines whether the changed display region is included in the reconstructed image data (step S108). If the changed display region is included in the reconstructed image data (Yes at step S108), the display control circuitry 373 then displays the high-resolution image data of the changed region (step S109).

On the other hand, if the changed display region is not included in the reconstructed image data (No at step S108), the reconstruction control circuitry 372 returns to step S105, and reconstructs the changed region with high resolution (step S105). If, at step S107, the display region is not changed (No at step S107), or when at step S109, the high-resolution image data of the changed region is displayed, the display control circuitry 373 determines whether a storage operation is executed (step S110).

Here, if the storage operation is not executed (No at step S110), the display control circuitry 373 returns to step S106, and displays the high-resolution image data. On the other hand, if the storage operation is executed (Yes at step S110), the control circuitry 37 stores the high-resolution image data in the image storage circuitry 36 (step S111), and completes the processing.

As described above, in the first embodiment, the input circuitry 31 receives a specifying operation of a certain region in the first medical image. The reconstruction control circuitry 372 then generates the second medical image having higher resolution than that of the first medical image from the image data used for generating the first medical image, for the certain region received by the input circuitry 31. The display control circuitry 373 then performs control so that the second medical image generated by the reconstruction control circuitry 372 is displayed on the display 32. Accordingly, the X-ray CT apparatus 1 according to the first embodiment can perform control so as to reconstruct the specified region with high resolution, and observe the entire region to be observed with higher resolution.

According to the first embodiment, the input circuitry 31 receives a specifying operation of a certain region in the image data collected three-dimensionally. Consequently, the X-ray CT apparatus 1 according to the first embodiment is capable of corresponding to the three-dimensional data.

According to the first embodiment, the input circuitry 31 receives a specifying operation of a region whose axis is parallel to the slice direction of the three-dimensional image data, or a region whose axis is in a direction having a certain angle relative to the slice direction of the three-dimensional image data, as a certain region. Consequently, the X-ray CT apparatus 1 according to the first embodiment, regardless of the arrangement of the portion of interest in the image data (for example, projection data), can perform control so as to reconstruct only a specified region with high resolution, and observe the entire region to be observed with high resolution.

According to the first embodiment, the reconstruction control circuitry 372 generates the second medical image for the peripheral region including the certain region received by the input circuitry 31. The display control circuitry 373, when the input circuitry 31 further receives a specifying operation of a region included in the peripheral region, performs control to display the region received by the input circuitry 31 by using the second medical image generated by the reconstruction control circuitry 372. Consequently, the X-ray CT apparatus 1 according to the first embodiment is capable of promptly responding to the adjustment of the region of interest.

According to the first embodiment, when the input circuitry 31 receives a specifying operation of a region whose axis is in a direction having a certain angle relative to the slice direction of the three-dimensional image data, the reconstruction control circuitry 372 sets a plurality of sub-regions in the direction parallel to the slice direction so as to include the region received in the specifying operation. The reconstruction control circuitry 372 then generates the second medical image corresponding to the region received in the specifying operation through the image data of each of the set sub-regions. Consequently, the X-ray CT apparatus 1 according to the first embodiment is capable of corresponding to the region of interest with the inclined Z'-axis, by applying zooming reconstruction.

According to the first embodiment, by executing back projection processing on the pixels corresponding to the certain region or the peripheral region including the certain region received by the input circuitry 31, the reconstruction control circuitry 372 generates the second medical image of the certain region or the peripheral region. Consequently, the X-ray CT apparatus 1 according to the first embodiment can directly reconstruct the region of interest with the inclined Z'-axis.

According to the first embodiment, the display control circuitry 373 displays the second medical image as well as the matrix size of the second medical image on the display 32. Consequently, the X-ray CT apparatus 1 according to the first embodiment can provide information on the high-resolution image data, and also give an indication on whether the image is stored and the like.

According to the first embodiment, the display control circuitry 373 displays positional information indicating the position of the certain region or the peripheral region in image data on the display 32. Consequently, the X-ray CT apparatus 1 according to the first embodiment can clarify the positional relation between the entire image and the display region such as the region of interest.

According to the first embodiment, the input circuitry 31 further receives a changing operation to change the size of the peripheral region. Consequently, the X-ray CT apparatus 1 according to the first embodiment can easily set a desired peripheral region.

Second Embodiment

In the first embodiment, the region of interest is first specified, and then the high-resolution reconstruction is executed on the specified region of interest. In a second embodiment, standard-resolution image data and high-resolution image data are generated in advance. In the second embodiment, the contents of image data stored in the image storage circuitry 36 and the processing contents of the reconstruction control circuitry 372 and the display control circuitry 373 are different from those in the first embodiment. Hereinafter, descriptions will be given mainly on these points.

The reconstruction control circuitry 372 according to the second embodiment generates a first medical image and a second medical image with different resolutions in advance, by generating medical images with different matrix sizes from image data. For example, the reconstruction control circuitry 372, when projection data is collected by scanning, controls the image reconstruction circuitry 35 so as to reconstruct a standard-resolution reconstructed image with a matrix size of "512×512" and a high-resolution reconstructed image with a matrix size of "4096×4096" in advance. The matrix sizes described above are merely examples, and the observer can arbitrarily set them.

The image storage circuitry 36 according to the second embodiment stores therein the standard-resolution reconstructed image and the high-resolution reconstructed image reconstructed by the control performed by the reconstruction control circuitry 372. The image storage circuitry 36 can also store therein a CT image (display image) generated from the reconstructed image.

The display control circuitry 373 according to the second embodiment reads out the second medical image at the position corresponding to a certain region in the first medical image received in a specifying operation by the input circuitry 31 from the image storage circuitry 36, and displays it on the display 32. Here, the display control circuitry 373 can also read out the second medical image at the position corresponding to the peripheral region including the certain region received in a specifying operation by the input circuitry 31 from the image storage circuitry 36, and displays it on the display 32.

Figure 12:
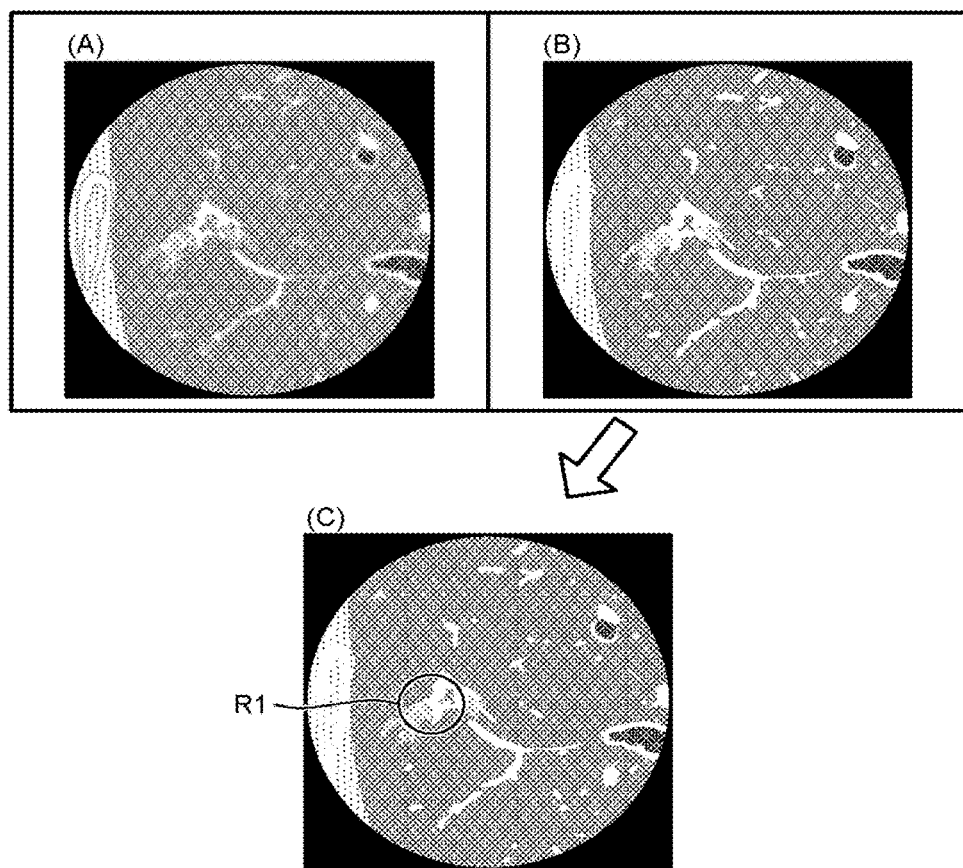
FIG. 12 is a schematic diagram for explaining an example of processing performed by the X-ray CT apparatus according to a second embodiment.
Figure 13:
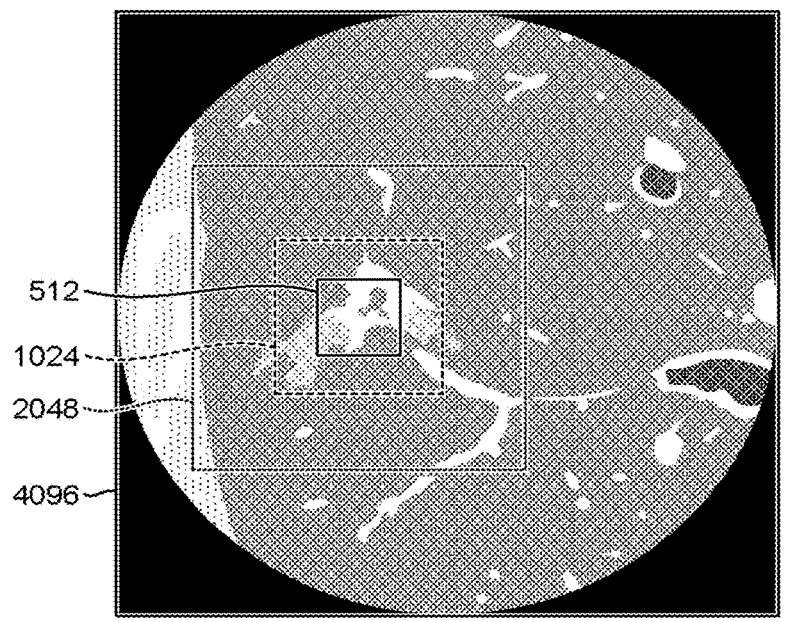
FIG. 13 is a schematic diagram for explaining an example of processing performed by the X-ray CT apparatus according to the second embodiment.

Hereinafter, with reference to FIG. 12 to FIG. 14, an example of processing performed by the X-ray CT apparatus 1 according to the second embodiment will be described. FIG. 12 to FIG. 14 are schematic diagrams for explaining examples of processing performed by the X-ray CT apparatus 1 according to the second embodiment. In the X-ray CT apparatus 1 according to the second embodiment, when scanning is executed and projection data is collected, as illustrated in (A) and (B) in FIG. 12, the reconstruction control circuitry 372 reconstructs the high-resolution reconstructed image and the standard-resolution reconstructed image, respectively.

As illustrated in (C) in FIG. 12, the display control circuitry 373 then displays the standard-resolution CT image on the display 32, and the input circuitry 31 receives a specifying operation of the region of interest R1. At this time, the input circuitry 31 can also receive a specifying operation of the peripheral region including the region of interest R1, in addition to the region of interest R1. The input circuitry 31 can also receive a changing operation to change the sizes of the region of interest R1 and the peripheral region.

Here, the display control circuitry 373 can perform control so as to display the matrix size of the second medical image on the display circuitry. For example, as illustrated in FIG. 13, the display control circuitry 373 displays matrix sizes of "512×512", "1024×1024", "2048×2048", and "4096×4096", on the standard-resolution CT image. Accordingly, the observer can identify the data size of the region of interest in advance.

As illustrated in (C) in FIG. 12, when the input circuitry 31 receives a specifying operation of the region of interest R1, the display control circuitry 373 reads out the high-resolution CT image at the position corresponding to the region of interest R1 from the image storage circuitry 36, and displays it on the display 32. At this time, for example, the display control circuitry 373 displays the change of the CT image of the region of interest R1 from the standard resolution to the high resolution. As an example, the display control circuitry 373, as illustrated in (A) in FIG. 14, displays the standard-resolution CT image until the high-resolution CT image is read out from the image storage circuitry 36, and when the reading of the high-resolution CT image is finished, as illustrated in (B) in FIG. 14, displays the high-resolution CT image on the display 32.

In the second embodiment, various methods described in the first embodiment are also applicable to the specifying operation of the region of interest R1 via the input circuitry 31.

Figure 15:
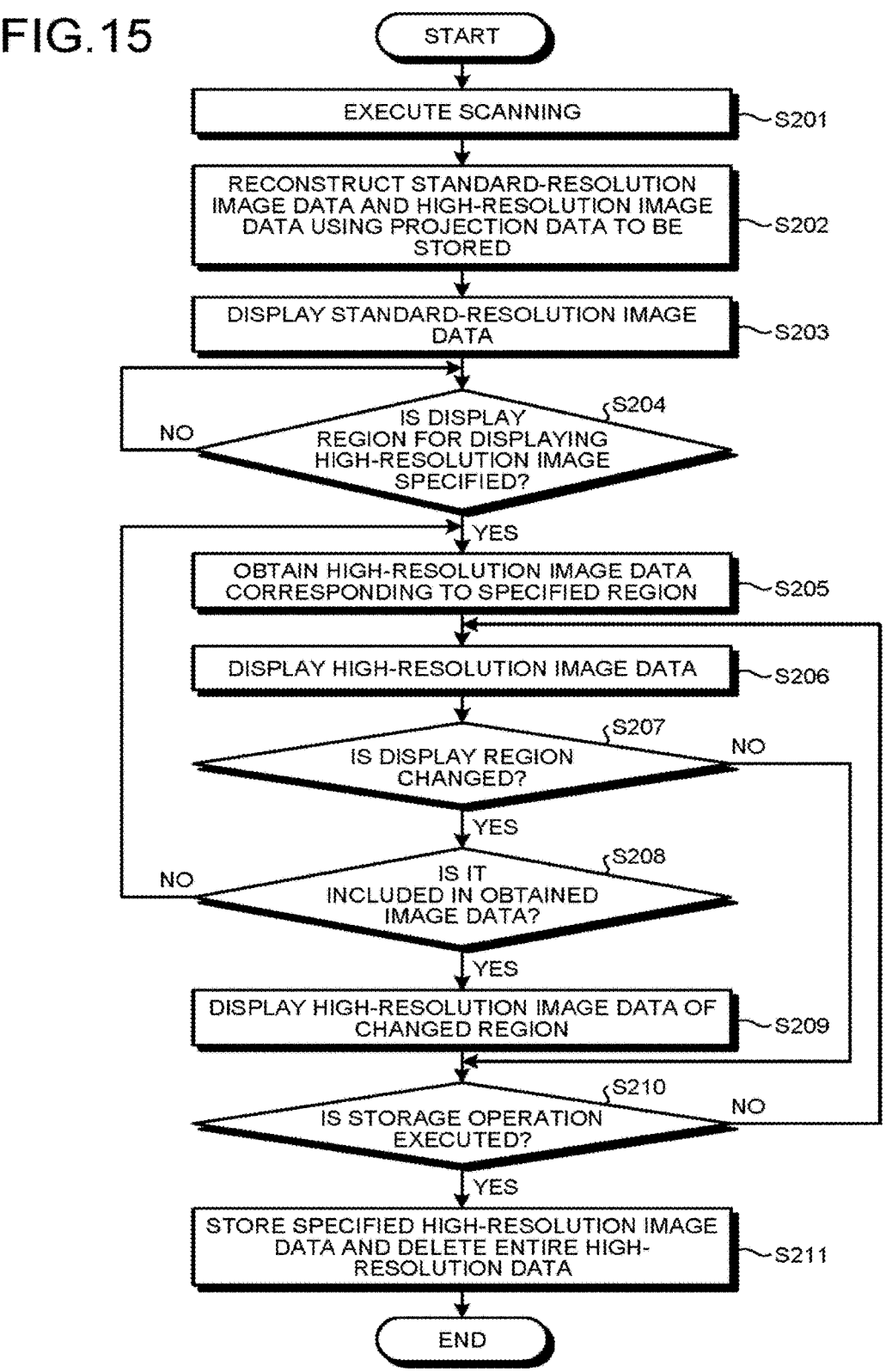
FIG. 15 is a flowchart for explaining an example of processing performed by the X-ray CT apparatus according to the second embodiment.

Next, with reference to FIG. 15, processing performed by the X-ray CT apparatus 1 according to the second embodiment will be described. FIG. 15 is a flowchart for explaining an example of processing performed by the X-ray CT apparatus 1 according to the second embodiment.

For example, as illustrated in FIG. 15, in the X-ray CT apparatus 1 according to the second embodiment, scanning is executed (step S201). Then, standard-resolution image data and high-resolution image data are reconstructed by using projection data and are stored (step S202). The display control circuitry 373 then displays the reconstructed standard-resolution image data on the display 32 (step S203).

The input circuitry 31 then determines whether the display region (for example, the region of interest R1) to display a high-resolution image is specified (step S204). If it is determined that the display region is specified (Yes at step S204), the display control circuitry 373 obtains the high-resolution image data corresponding to the specified region (step S205). The display control circuitry 373 then displays the obtained high-resolution image data on the display 32 (step S206), and determines whether the display region is changed (step S207).

If the display region is changed (Yes at step S207), the display control circuitry 373 determines whether the changed display region is included in the obtained image data (step S208). Here, if the changed display region is included in the obtained image data (Yes at step S208), the display control circuitry 373 displays the high-resolution image data of the changed region (step S209).

On the other hand, if the changed display region is not included in the obtained image data (No at step S208), the reconstruction control circuitry 372 returns to step S205, and obtains the high-resolution image data of the changed region (step S205). If at step S207, the display region is not changed (No at step 207), or when at step S209, the high-resolution image data of the changed region is displayed, the display control circuitry 373 determines whether a storage operation is executed (steps S210).

Here, if the storage operation is not executed (No at step S210), the display control circuitry 373 returns to step S206, and displays the high-resolution image data. On the other hand, if the storage operation is executed (Yes at step S210), the control circuitry 37 stores the specified high-resolution image data in the image storage circuitry 36, deletes the entire high-resolution image data (step S211), and completes the processing.

As described above, according to the second embodiment, the image storage circuitry 36 stores therein the first medical image and the second medical image generated by the reconstruction control circuitry 372. The reconstruction control circuitry 372, by generating medical images with different matrix sizes from image data, generates the first medical image and the second medical image with different resolutions in advance. Accordingly, the X-ray CT apparatus 1 according to the second embodiment can promptly respond to the specifying operation, by generating and storing the pieces of image data with different resolutions in advance.

According to the second embodiment, the display control circuitry 373 reads out the second medical image at the position corresponding to a certain region in the first medical image received in the specifying operation by the input circuitry 31 from the image storage circuitry 36, and displays it on the display 32. Consequently, the X-ray CT apparatus 1 according to the second embodiment is capable of promptly providing high-resolution image data at the timing desired by the observer.

According to the second embodiment, the display control circuitry 373 performs control so as to read out the second medical image at the position corresponding to the peripheral region including the certain region received in the specifying operation by the input circuitry 31, from the image storage circuitry 36, and display it on the display 32. Consequently, the X-ray CT apparatus 1 according to the second embodiment is capable of flexibly responding to the specifying operation desired by the observer.

According to the second embodiment, the input circuitry 31 further receives a changing operation to change the size of the peripheral region. Consequently, the X-ray CT apparatus 1 according to the second embodiment can change the peripheral region depending on the situation.

According to the second embodiment, the display control circuitry 373 performs control to display the matrix size of the second medical image on the display 32. Consequently, the X-ray CT apparatus 1 according to the second embodiment allows the observer to identify the data size of the high-resolution image data.

Third Embodiment

While the first and second embodiments have been described above, it is to be understood that various modifications may be made in addition to the first and second embodiments described above.

Figure 16:
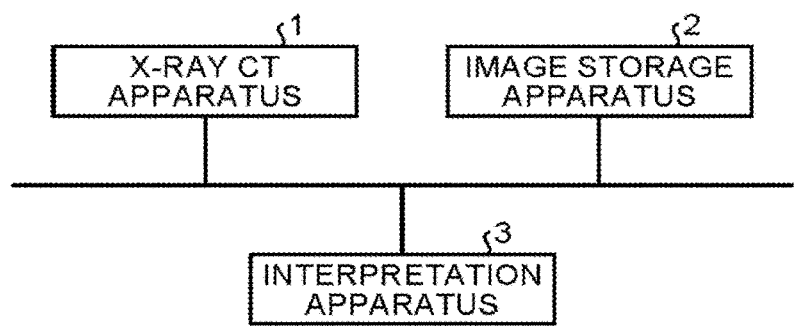
FIG. 16 is a configuration example of an image display system according to a third embodiment.

In the embodiments described above, the X-ray CT apparatus as a medical image diagnostic apparatus displays a standard-resolution CT image and a high-resolution CT image. However, embodiments are not limited thereto, and for example, an interpretation apparatus connected to a network, to which a medical image diagnostic apparatus is connected, may display the standard-resolution medical image and the high-resolution medical image. FIG. 16 is a configuration example of an image display system according to a third embodiment.

As illustrated in FIG. 16, the image display system includes the X-ray CT apparatus 1, an image storage apparatus 2, and an interpretation apparatus 3. The respective apparatus illustrated in FIG. 16, for example, can communicate with one another either directly or indirectly via an in-hospital local area network (LAN) installed in a hospital. For example, when a picture archiving and communication system (PACS) is installed in the image display system, the respective apparatus receive and transmit medical images and the like from and to one another, according to the Digital Imaging and Communications in Medicine (DICOM) standard.

The X-ray CT apparatus 1 executes the processes described in the first and second embodiments. More specifically, the X-ray CT apparatus 1 transmits a standard-resolution CT image and a high-resolution CT image to the interpretation apparatus 3, corresponding to a request received from the interpretation apparatus 3. The image storage apparatus 2 is a database that stores medical images. More specifically, the image storage apparatus 2 stores a CT image and the like transmitted from the X-ray CT apparatus 1 or the interpretation apparatus 3 in a storage circuitry. The interpretation apparatus 3 is a device used by the observer to read a medical image such as a CT image, and for example, a workstation and a terminal apparatus.

An example of applying the first embodiment to the image display system according to the third embodiment will now be described. In such a case, after the X-ray CT apparatus 1 executes scanning and collects projection data, the X-ray CT apparatus 1 reconstructs a standard-resolution CT image and transmits it to the interpretation apparatus 3. The interpretation apparatus 3 displays the received CT image on a monitor. The observer then executes a specifying operation of the region of interest and the peripheral region on the standard-resolution CT image displayed on the monitor. Here, the observer selects the region of interest and the peripheral region by using various methods explained in the first embodiment described above. The interpretation apparatus 3, on receiving the specifying operation, transmits positional information of the region on the CT image to the X-ray CT apparatus 1.

The X-ray CT apparatus 1, from the positional information of the region of interest and the peripheral region received in the specifying operation by the interpretation apparatus 3, reconstructs a high-resolution CT image for the selected region, and transmits it to the interpretation apparatus 3. At this time, the matrix size of the high-resolution CT image reconstructed by the X-ray CT apparatus 1 according to the present embodiment is about the same as that (for example, 512×512) of a conventional one. Consequently, it is possible to provide a high-resolution image without imposing a burden on the network and the interpretation apparatus 3.

Next, an example of applying the second embodiment to the image display system according to the third embodiment will be described. In such a case, after the X-ray CT apparatus 1 executes scanning and collects projection data, the X-ray CT apparatus 1 reconstructs a standard-resolution CT image and a high-resolution CT image and stores them in the image storage circuitry 36 included therein. The X-ray CT apparatus 1 then transmits the standard-resolution CT image to the interpretation apparatus 3. The interpretation apparatus 3 displays the received CT image on a monitor. The observer executes a specifying operation of the region of interest and the peripheral region on the standard-resolution CT image displayed on the monitor. Here, the observer selects the region of interest and the peripheral region by using various methods explained in the first embodiment described above. The interpretation apparatus 3, on receiving the specifying operation, transmits the positional information of the region on the CT image to the X-ray CT apparatus 1.

The X-ray CT apparatus 1, from the positional information of the region of interest and the peripheral region received in the specifying operation by the interpretation apparatus 3, obtains a high-resolution CT image at the position corresponding to the selected region, and transmits it to the interpretation apparatus 3. At this time, the matrix size of the high-resolution CT image reconstructed by the X-ray CT apparatus 1 according to the present embodiment is large (for example, 4096×4096). However, the CT image actually to be transmitted or received is only the selected region and the data size is small. Consequently, it is possible to provide a high-resolution image without imposing a burden on the network and the interpretation apparatus 3.

In either event, when the first embodiment is applied or the second embodiment is applied, the CT image stored in high resolution is only a limited region. Accordingly, for example, it is possible to reduce a burden imposed on the image storage circuitry 36 in the X-ray CT apparatus 1 and the storage capacity of the image storage apparatus 2.

In the embodiments described above, the X-ray CT apparatus is used as an example of the medical image diagnostic apparatus. However, embodiments are not limited thereto, and for example, a magnetic resonance imaging (MRI) apparatus may be used.

The constituents of each of the apparatus illustrated in the first embodiment to the third embodiment described above are functionally conceptual, and are not necessarily required to be physically configured as illustrated. In other words, the specific mode of dispersion and integration of each apparatus is not limited to the ones illustrated in the drawings, and all or a part thereof can be functionally or physically dispersed or integrated in an optional unit, depending on various kinds of load and the status of use. All or an optional part of the respective processing functions carried out in each apparatus are implemented by a CPU and a computer program analyzed and executed by the CPU, or may be implemented as hardware by the wired logic.

The control methods described in the first to third embodiments may be implemented by executing a control program prepared in advance by a computer such as a personal computer and a workstation. The control program may be distributed via a network such as the Internet. The control program may also be recorded on a computer-readable recording medium such as a hard disk, a flexible disk (FD), compact disc read-only memory (CD-ROM), a magneto-optical (MO), and a digital versatile disc (DVD), and executed by being read out from the recording medium by a computer.

As described above, according to the first to third embodiments, it is possible to easily observe the entire region to be observed with higher resolution.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography (CT) apparatus, comprising:
    an X-ray tube configured to emit an X-ray;
    a detector configured to detect the X-ray emitted from the X-ray tube and having passed through a subject;
    processing circuitry configured to
        collect projection data, based on detection data detected by the detector, reconstruct a reconstructed image data, based on the projection data;
    a display configured to display a display image based on the reconstructed image data; and
    input circuitry configured to receive an operation to rotate a first display image based on a first reconstructed image data reconstructed by the processing circuitry on a display screen of the display, and specify a three-dimensional region on a second display image whose axis is in a direction different from a slice direction,
    wherein
    the processing circuitry is configured to reconstruct a second reconstructed image data based on the projection data so as to have higher resolution than that of the first display image, for the three-dimensional region.

2. The X-ray CT apparatus according to claim 1, wherein the display image is a volume rendering image.

3. The X-ray CT apparatus according to claim 1, wherein the display image is an MIP image whose normal direction relative to the display screen is in a line of sight.

4. The X-ray CT apparatus according to claim 1, wherein when the three-dimensional region in a two-dimensional manner is specified in a horizontal direction relative to the display screen on the second display image, the input circuitry is configured to set the three-dimensional region capable of reconstructing the second reconstructed image data that has higher resolution than that of the first display image on the projection data, based on the three-dimensional region.

5. The X-ray CT apparatus according to claim 4, wherein the three-dimensional region is a prism or a cylinder.

6. The X-ray CT apparatus according to claim 1, wherein the display is configured to display the second display image and the three-dimensional region simultaneously on the display screen.

7. The X-ray CT apparatus according to claim 1, wherein the input circuitry is configured to receive an operation to specify a three-dimensional region on image data collected three-dimensionally.

8. The X-ray CT apparatus according to claim 7, wherein the input circuitry is configured to receive an operation to specify a region whose axis is in a direction parallel to a slice direction of three-dimensional image data, or a region whose axis is in a direction having a certain angle relative to the slice direction of the three-dimensional image data, as the three-dimensional region on image data.

9. The X-ray CT apparatus according to claim 1, wherein the processing circuitry is configured to reconstruct the second reconstructed image data of a peripheral region including the three-dimensional region received by the input circuitry, and
    when the input circuitry further receives a specifying operation of a region included in the peripheral region, the display is configured to display the display image of the region received by the input circuitry by using the second reconstructed image data reconstructed by the processing circuitry.

10. The X-ray CT apparatus according to claim 9, wherein the input circuitry is further configured to receive a changing operation to change a size of the peripheral region.

11. The X-ray CT apparatus according to claim 1, wherein when the input circuitry receives an operation to specify a region whose axis is in a direction different from the slice direction, the processing circuitry is configured to set a plurality of sub-regions in a direction parallel to the slice direction so as to include the region received in the specifying operation, and reconstruct the second reconstructed image data corresponding to the region received in the specifying operation from image data of each of the set sub-regions.

12. The X-ray CT apparatus according to claim 1, wherein the processing circuitry is configured to, by executing back projection processing relative to a pixel corresponding to a region received by the input circuitry, reconstruct the second reconstructed image data of the region.

13. The X-ray CT apparatus according to claim 1, wherein the display is configured to display the display image based on the second reconstructed image data and display a matrix size of the second reconstructed image data.

14. The X-ray CT apparatus according to claim 1, wherein the display is configured to display positional information indicating a position of a region received by the input circuitry in the first reconstructed image data.

15. The X-ray CT apparatus according to claim 1, further comprising
a storage circuitry configured to store therein the reconstructed image data reconstructed by the processing circuitry, wherein
the processing circuitry is configured to, by reconstructing the reconstructed image data of a different matrix size from the projection data, the first reconstructed image data and the second reconstructed image data with different resolutions in advance.

16. The X-ray CT apparatus according to claim 15, wherein the display is configured to display the display image by reading out the second reconstructed image data at a position corresponding to the three-dimensional region in the first reconstructed image data received by the input circuitry from the storage circuitry.

17. The X-ray CT apparatus according to claim 15, wherein the display is configured to display the display image by reading out the second reconstructed image data at a position corresponding to a peripheral region including the three-dimensional region received by the input circuitry from the storage circuitry.

18. The X-ray CT apparatus according to claim 17, wherein the input circuitry is further configured to receive a changing operation to change a size of the peripheral region.

19. The X-ray CT apparatus according to claim 15, wherein the display is configured to display a matrix size of the second reconstructed image data.

20. The X-ray CT apparatus according to claim 1, wherein the input circuitry is configured to receive the operation to specify the three-dimensional region whose axis is in a direction different from the slice direction on the second display image which is an image after the first display image has been rotated.

21. An image diagnostic apparatus, comprising:
processing circuitry configured to reconstruct a reconstructed image data;
a display configured to display a display image based on the reconstructed image data; and
input circuitry configured to receive an operation to rotate a first display image based on a first reconstructed image data reconstructed by the processing circuitry on a display screen of the display, and specify a three-dimensional region on a second display image whose axis is in a direction different from a slice direction, wherein
the processing circuitry is configured to reconstruct a second reconstructed image data so as to have higher resolution than that of the first display image, for the three-dimensional region.

* * * * *